United States Patent
Yu et al.

(10) Patent No.: US 10,613,160 B2
(45) Date of Patent: Apr. 7, 2020

(54) CRYOCOOLED SQUID MEASUREMENT APPARATUS

(71) Applicant: Korea Research Institute of Standards and Science, Daejeon (KR)

(72) Inventors: Kwon-Kyu Yu, Daejeon (KR);
Kiwoong Kim, Daejeon (KR);
Hyukchan Kwon, Daejeon (KR);
Jin-Mok Kim, Daejeon (KR); Sang-Kil Lee, Daejeon (KR); Yong-Ho Lee, Daejeon (KR)

(73) Assignee: Korea Research Institute of Standards and Science, Daejeon (KR)

(*) Notice: Subject to any disclaimer, the term of this patent is extended or adjusted under 35 U.S.C. 154(b) by 295 days.

(21) Appl. No.: 15/445,275

(22) Filed: Feb. 28, 2017

(65) Prior Publication Data

US 2017/0168121 A1 Jun. 15, 2017

Related U.S. Application Data

(63) Continuation of application No. PCT/KR2015/009114, filed on Aug. 31, 2015.

(30) Foreign Application Priority Data

Sep. 5, 2014 (KR) .................. 10-2014-0119290

(51) Int. Cl.
*F25B 9/14* (2006.01)
*G01R 33/00* (2006.01)
(Continued)

(52) U.S. Cl.
CPC ........ *G01R 33/007* (2013.01); *A61B 5/04008* (2013.01); *A61B 5/05* (2013.01);
(Continued)

(58) Field of Classification Search
CPC ... F25B 9/10; F25B 9/14; F25B 9/145; G01R 33/007; G01R 33/0354
See application file for complete search history.

(56) References Cited

U.S. PATENT DOCUMENTS 5,737,927 A * 4/1998 Takahashi ............. F25D 19/006
62/383
6,230,499 B1 * 5/2001 Hohne .................... F25B 9/145
374/E17.003
(Continued)

FOREIGN PATENT DOCUMENTS

JP 06-014899 A 1/1994
JP 07-321382 A 12/1995
(Continued)

OTHER PUBLICATIONS

Korean Office Action for Application No. 10-2014-0119290 dated Sep. 15, 2015.
(Continued)

*Primary Examiner* — Brian M King
(74) *Attorney, Agent, or Firm* — Jenkins, Wilson, Taylor & Hunt, P.A.

(57) ABSTRACT

A cryocooler superconducting quantum interference (SQUID) system includes a cryocooler including a cold head, a cold head chamber in which the cold head is disposed, a sensor chamber including a SQUID sensor cooled to a low temperature by the cryocooler; and a connection block connecting the cold head and a thermal anchor disposed in the sensor chamber to each other to cool the SQUID sensor in the sensor chamber.

22 Claims, 22 Drawing Sheets

(51) Int. Cl.
  *G01R 33/035* (2006.01)
  *A61B 5/05* (2006.01)
  *F25D 19/00* (2006.01)
  *A61B 5/04* (2006.01)
  *F25B 9/10* (2006.01)
  *A61B 5/00* (2006.01)

(52) U.S. Cl.
  CPC ............ *F25B 9/145* (2013.01); *F25D 19/006* (2013.01); *G01R 33/0076* (2013.01); *G01R 33/035* (2013.01); *G01R 33/0354* (2013.01); *A61B 5/0046* (2013.01); *A61B 5/04007* (2013.01); *F25B 9/10* (2013.01); *F25B 2309/1412* (2013.01)

(56) References Cited

U.S. PATENT DOCUMENTS 6,332,324 B1* 12/2001 Saho .................. F17C 3/02
  62/383

2006/0225437 A1* 10/2006 Kazami .................. F25B 9/14
  62/51.1
2016/0223622 A1* 8/2016 Yu .......................... G01R 33/035

FOREIGN PATENT DOCUMENTS

JP    2005-291629 A    10/2005
KR    10-2002-0088588 A    11/2002

OTHER PUBLICATIONS

Korean Office Action for Application No. 10-2014-0119290 dated Mar. 22, 2016.
Grant of Patent for Korean Application No. 10-2014-0119290 dated May 13, 2016.
IPRP with Written Opinion for Application No. PCT/KR2015/009114 dated Mar. 7, 2017.
International Search Report for Application No. PCT/KR2015/009114 dated Dec. 9, 2015.

* cited by examiner

CRYOCOOLED SQUID MEASUREMENT APPARATUS

CROSS-REFERENCE TO RELATED APPLICATIONS

This application is a continuation of and claims priority to PCT/KR2015/009114 filed on Aug. 31, 2015, which claims priority to Korea Patent Application No. 10-2014-0119290 filed on Sep. 5, 2014, the entireties of which are both incorporated by reference herein.

TECHNICAL FIELD

The present disclosure relates to cryocooler superconducting quantum interference device (SQUID) systems and, more particularly, to a cryocooler SQUID system using a direct cooling technique.

BACKGROUND

A superconducting quantum interference device (SQUID) is used to measure very fine magnetic signals of several tens to several hundreds of femtotesla (fT) which are generated by human activities of brain, heart, muscles, and the like. In particular, the SQUID may be medically used in brain function mapping, disease diagnosis of localization of an epilepsy occurrence position, and cognitive function diagnosis by analyzing magnetic signals generated from the brain. However, the SQUID should be cooled to −265 degrees Celsius to operate a SQUID sensor.

In a cooling method that is currently used commercially, a sensor is directly cooled using liquid helium. However, the maintenance cost of a magnetoencephalography (MEG) apparatus is rapidly increasing with supply and demand instability of helium gas which results from global exhaustion of fossil resources. In addition, a user and a subject may be exposed to a very dangerous environment when they treat a cryogenic coolant of −270 degrees Celsius. To overcome these disadvantages, a SQUID apparatus for measuring a biomagnetism using a cryocooling technique has been actively developed.

Coolers have various cooling types such as pulse tube type, Gilfford-Macmahon type, and Joule-Thompson type. Materials used in a regenerator of a cryocooler are $Er_3Ni$, Pb, and the like, which generate a cyclic magnetic noise according to a high-pressure pulse as they are magnetized by their phase changes depending on temperature change. The generated cyclic magnetic noise has several hundreds of micro Tesla and is several to hundreds of thousands times greater than a biomagnetic signal desired to be measured. The magnetic noise distorts a signal to have a great influence on signal analysis.

An indirect cooling technique uses a metal having a high thermal conductivity to effectively transfer heat from a cryocooler to a SQUID sensor. Thus, a thermal noise generated from the metal may significantly reduce operation stability and sensitivity of a SQUID apparatus.

In an existing developed cryocooled SQUID apparatus, a SQUID sensor and a cold head of a cryocooler are integrated into one body. After a cyclic magnetic noise generated from the cold head is removed using a first-order gradiometer or a second-order gradiometer, and a remaining magnetic noise is removed using a digital filter. A signal processed with the digital filter may cause information distortion or loss. Moreover, since a thermal noise generated from a metal has no constant cyclicity, the thermal noise cannot be removed using the digital filter. Thus, sensitivity and stability of the SQUID apparatus are restricted.

After a typical SQUID apparatus using liquid helium is cooled using a coolant, it is very difficult to change a shape or a position of the typical SQUID apparatus. Thus, cognitive function measurement according to a subject's posture and measurement for disease diagnosis cannot be performed using only one apparatus. When a cryocooling technique is introduced to address this shortcoming, structural change is required.

A supersensitive SQUID sensor has been used in various applications such as medical, defense, resource exploration, and space exploration. In particular, the supersensitive SQUID sensor has been actively used in medical fields such as disease diagnosis and brain activity research by measuring a fine magnetism generated from heart and brain. However, high-priced liquid helium should be used to operate a low-temperature SQUID sensor and a special magnetically shielded room having a high magnetic shielding rate is required to reduce an environmental noise and an earth magnetic field that is millions of times greater than an MEG signal. These two problems act as great limitation when a SQUID system is used in a medical field.

Accordingly, various techniques have been developed to reduce consumption of liquid helium. For example, using a closed cycle cryocooler, a helium (He) circulation system is developed, a thermal shield of a low-temperature coolant storage container is cooled or a SQUID sensor is directly cooled.

Daikin Corporation directly cooled a SQUID system using a GM-type cryocooler, instead of liquid helium, to measure a magnetocardiography (MCG) signal and a magnetoencephalography (MEG) signal. However, many added averages and digital signal processes should be used due to an influence of a magnetic noise caused by a cycle noise of the cryocooler. As a result, disadvantages such as signal loss and distortion occur.

SUMMARY

To overcome the above disadvantages, according to an example embodiment of the present disclosure, a cold head chamber including a regenerator is separated from a sensor chamber on which a SQUID sensor is mounted. The SQUID sensor removes cyclic magnetic noise and thermal noise by using a superconductive shield.

In addition, by using a Permalloy, a ferromagnetic shield prevents a cyclic magnetic noise generated from the cryocooler of the cold head chamber from being exposed to the outside.

In addition, the separated cold head chamber is mounted outside a magnetically shielded room to be completely separated magnetically or spatially from the SQUID sensor.

Example embodiments of the present disclosure provide an effective cooling method of a SQUID sensor using a cryocooler and a superconductive shield.

Example embodiments of the present disclosure provide removal of cyclic magnetic noise and thermal noise generated from a cryocooler.

Example embodiments of the present disclosure provide a SQUID system capable of providing position change of a SQUID sensor.

Example embodiments of the present disclosure provide a cooling method of a SQUID sensor and a SQUID system including a superconductive shield for removing cyclic magnetic noise generated from a cryocooler.

A cryocooler superconducting quantum interference device (SQUID) system according to an example embodiment of the present disclosure includes: a cryocooler including a cold head; a cold head chamber in which the cold head is disposed; a sensor chamber including a SQUID sensor cooled to a low temperature by the cryocooler; and a connection block connecting the cold head and a thermal anchor disposed in the sensor chamber to each other to cool the SQUID sensor in the sensor chamber.

In an example embodiment, the cryocooler SQUID system may further include: a cold head magnetic shield formed of permalloy disposed to surround the cold head inside or outside the cold head chamber.

In an example embodiment, the cryocooler may be a pulse tube cryocooler. The cryocooler may include a first stage cold head cooled to a first temperature (40 K) and a second stage cold head cooled to a second temperature (4 K).

In an example embodiment, the cryocooler SQUID system may further include: a tube-shaped thermal transfer tube disposed inside the connection block and connecting the first cold head and a first thermal anchor disposed in the sensor chamber to each other; and a rod-shaped thermal transfer rod disposed inside the thermal transfer tube and connecting the second stage cold head and a second thermal anchor disposed in the sensor chamber to each other.

In an example embodiment, the connection block may include: a first elbow block connected to the cold head chamber; a straight block connected to the first elbow block; a second elbow block connected to the straight block; an elbow-shaped first thermal transfer tube disposed inside the first elbow block and the straight block; an L-shaped first thermal transfer rod disposed inside the first thermal transfer tube and the straight block; an elbow-shaped second thermal transfer tube disposed inside the second elbow block; and an L-shaped second thermal transfer rod disposed inside the second thermal transfer tube. The second elbow block may be connected to the sensor chamber.

In an example embodiment, the first thermal transfer tube and the second thermal transfer tube may be connected by a braided copper wire, and the first thermal transfer rod and the second thermal transfer rod may be connected by a braided copper wire.

In an example embodiment, the cryocooler SQUID system may further include: a rotation flange disposed at a portion where the first thermal transfer tube and the second thermal transfer tube are connected to each other and providing a rotational motion to the second elbow block and the sensor chamber fixed to each other.

In an example embodiment, one end of the rotation flange may be in the form of a tapered tube inserted into the straight block. A groove may be formed on a surface of the tapered tube to maintain a vacuum state.

In an example embodiment, the cryocooler SQUID system may further include: an internal adiabatic layer disposed between the thermal transfer rod and the thermal transfer tube; and an external adiabatic layer disposed between the thermal transfer tube and the connection block.

In an example embodiment, the cryocooler SQUID system may further include: a space maintaining portion formed of an adiabatic material and disposed between the thermal transfer rod and the thermal transfer tube to maintain a fixed distance.

In an example embodiment, the space maintaining portion may include: a pair of star-shaped spacers inserted into opposite ends of a straight portion of the thermal transfer rod; and a plurality of rod-shaped spacer supports connecting the pair of spacers to each other.

In an example embodiment, the cryocooler SQUID system may further include: a washer-shaped first thermal anchor disposed in the sensor chamber and connected to the thermal transfer tube; a washer-shaped second thermal anchor disposed in the sensor chamber and connected to the thermal transfer rod; a cylindrical first thermal shield connected to the first thermal anchor and extending in a central axis direction of the sensor chamber; and a cylindrical second thermal shield disposed inside the first thermal shield, connected to the second thermal anchor, and extending in the central axis direction of the sensor chamber.

In an example embodiment, the cryocooler SQUID system may further include: a pair of washer-shaped auxiliary thermal anchors disposed between the first thermal anchor and the second thermal anchor; and an auxiliary thermal transfer portion inserted between the pair of auxiliary thermal anchors to extend in the central axis direction of the sensor chamber and formed of a copper mesh.

In an example embodiment, the cryocooler SQUID system may further include: a superconductive shield disposed around the SQUID sensor to remove an external noise and formed of a superconductor.

In an example embodiment, the cold head chamber accommodating the cold head may be separated from the sensor chamber accommodating the SQUID sensor.

In an example embodiment, the cold head chamber, the connection block, and the sensor chamber may be maintained in a vacuum state.

In an example embodiment, the superconductive shield may be in the form of a helmet. The cryocooler SQUID system may further include: a SQUID sensor-mounted helmet disposed inside the superconductive shield; a first thermal cap cooled to a temperature of 40 K, disposed to cover the SQUID sensor, and formed of a copper mesh molded in the form of a helmet; and a second thermal cap cooled to a temperature of 4 K, disposed between the first thermal cap and the SQUID sensor-mounted helmet, and formed of a copper mesh molded in the form of a helmet.

In an example embodiment, the superconductive shield may include: a hemispherical superconductive helmet body; an outer brim extending from a bottom surface to an outer side of the superconductive helmet body; and an inner brim extending from the bottom surface to an inner side of the superconductive helmet body.

In an example embodiment, the cold head chamber may be disposed outside a magnetically shielded room. The sensor chamber may be disposed inside the magnetically shield room.

In an example embodiment, the cold head chamber and the sensor chamber may be disposed inside a magnetically shielded room.

In an example embodiment, the connection block may be a bellows to reduce a vibration.

In an example embodiment, the cryocooler SQUID system may further include: a thermal transfer portion thermally connecting the cold head and the thermal anchor to each other. The thermal transfer portion may be flexible braided copper wires.

In an example embodiment, a length of the flexible braided copper wires may be 1 meter or longer.

In an example embodiment, the first stage cold head may be connected to a 40 K first thermal anchor by a first thermal transfer portion, and the second stage cold head may be connected to a 4K second thermal anchor by a second thermal transfer portion. The first and second thermal transfer portions may be flexible braided copper wires.

A cryocooler superconducting quantum interference device (SQUID) system according to an example embodiment of the present disclosure includes: a cryocooler including a cold head; a cold head chamber in which the cold head is disposed; and a sensor chamber including a SQUID sensor cooled to a low temperature by the cryocooler. The cold head chamber accommodating the cold head may be separated from the sensor chamber accommodating the SQUID sensor.

In an example embodiment, the cryocooler SQUID system may further include: a connection block connecting the cold head chamber and the sensor chamber to each other. The connection block may include at least one elbow block bent at an angle of 90 degrees.

In an example embodiment, a distance between the cold head chamber and the sensor chamber may be 1 meter or longer.

In an example embodiment, the cryocooler SQUID system may further include: a cold head magnetic shield disposed to cover the cold head and formed of permalloy.

In an example embodiment, the cryocooler SQUID system may further include: a superconductive shield disposed in the sensor chamber, disposed around the SQUID sensor to shield a magnetic noise, and formed of a superconductor.

A cryocooler superconducting quantum interference device (SQUID) system according to an example embodiment of the present disclosure includes: a cryocooler including a cold head; a cold head chamber in which the cold head is disposed; a cold head magnetic shield disposed to cover the cold head and formed of a ferromagnetic material; and a sensor chamber including a SQUID sensor cooled to a low temperature by the cryocooler.

In an example embodiment, the cold head magnetic shield may be disposed inside the cold head chamber.

In an example embodiment, the cold head magnetic shield may be permalloy.

In an example embodiment, the cold head magnetic shield may be disposed to cover a first stage of the cold head cooled to a first temperature and a second stage of the cold head cooled to a second temperature higher than the first temperature.

In an example embodiment, the cold head magnetic shield may be Mu-metal of a nickel-iron alloy.

In an example embodiment, the cold head chamber may be disposed outside a magnetically shielded room shielding an external magnetic field. The sensor chamber may be disposed inside the magnetically shielded room.

In an example embodiment, the cryocooler SQUID system may further include: a superconductive shield disposed around the SQUID sensor to remove an external noise and formed of a superconductor.

A cryocooler superconducting quantum interference device (SQUID) system according to an example embodiment of the present disclosure includes: a cryocooler including a cold head; a cold head chamber in which the cold head is disposed; a sensor chamber including a SQUID sensor cooled to a low temperature by the cryocooler; and a superconductive shield disposed in the sensor chamber, disposed around the SQUID sensor to shield a magnetic noise in the sensor chamber, and formed of a superconductor. The cold head chamber accommodating the cold head is separated from the sensor chamber accommodating the SQUID sensor.

In an example embodiment, the cryocooler SQUID system may further include: a cold head magnetic shield disposed to cover the cold head and formed of permalloy.

In an example embodiment, the cryocooler SQUID system may further include: a connection block connecting the cold head and a thermal anchor disposed in the sensor chamber to each other to cool the SQUID sensor.

In an example embodiment, the cryocooler SQUID system may further include: a SQUID sensor-mounted helmet disposed inside the sensor chamber; and a rotational motion driver providing a position change of the sensor chamber to measure a magnetoencephalography (MEG) signal according to a subject's posture.

A cryocooler superconducting quantum interference device (SQUID) system according to an example embodiment of the present disclosure includes: a cryocooler including a cold head; a cold head chamber in which the cold head is disposed; a sensor chamber including a SQUID sensor cooled to a low temperature by the cryocooler; and a rotational motion driver providing a position change of the sensor chamber to measure a magnetoencephalography (MEG) signal according to a subject's posture.

In an example embodiment, the rotational motion driver may rotate a central shaft of the sensor chamber at an angle between directions vertical and horizontal to the ground.

In an example embodiment, the cryocooler SQUID system may further include: a connection block connecting the cold head chamber and the sensor chamber to each other. The connection block may include two elbow blocks bent at an angle of 90 degrees.

In an example embodiment, the rotational motion driver may provide a rotational motion to the elbow block. The rotational motion driver may include: a worm gear rotation shaft connected to the second elbow block and horizontal to the ground, a worm gear disposed at the work gear rotation shaft, a worm gearing with the worm gear, a worm rotation shaft where the worm is formed, a first bevel gear disposed at the worm rotation shaft, a second bevel gear gearing with the first bevel gear, and a bevel gear rotation shaft combined with the second bevel gear.

BRIEF DESCRIPTION OF THE DRAWINGS

The present disclosure will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the present disclosure.

DETAILED DESCRIPTION

Figure 1:
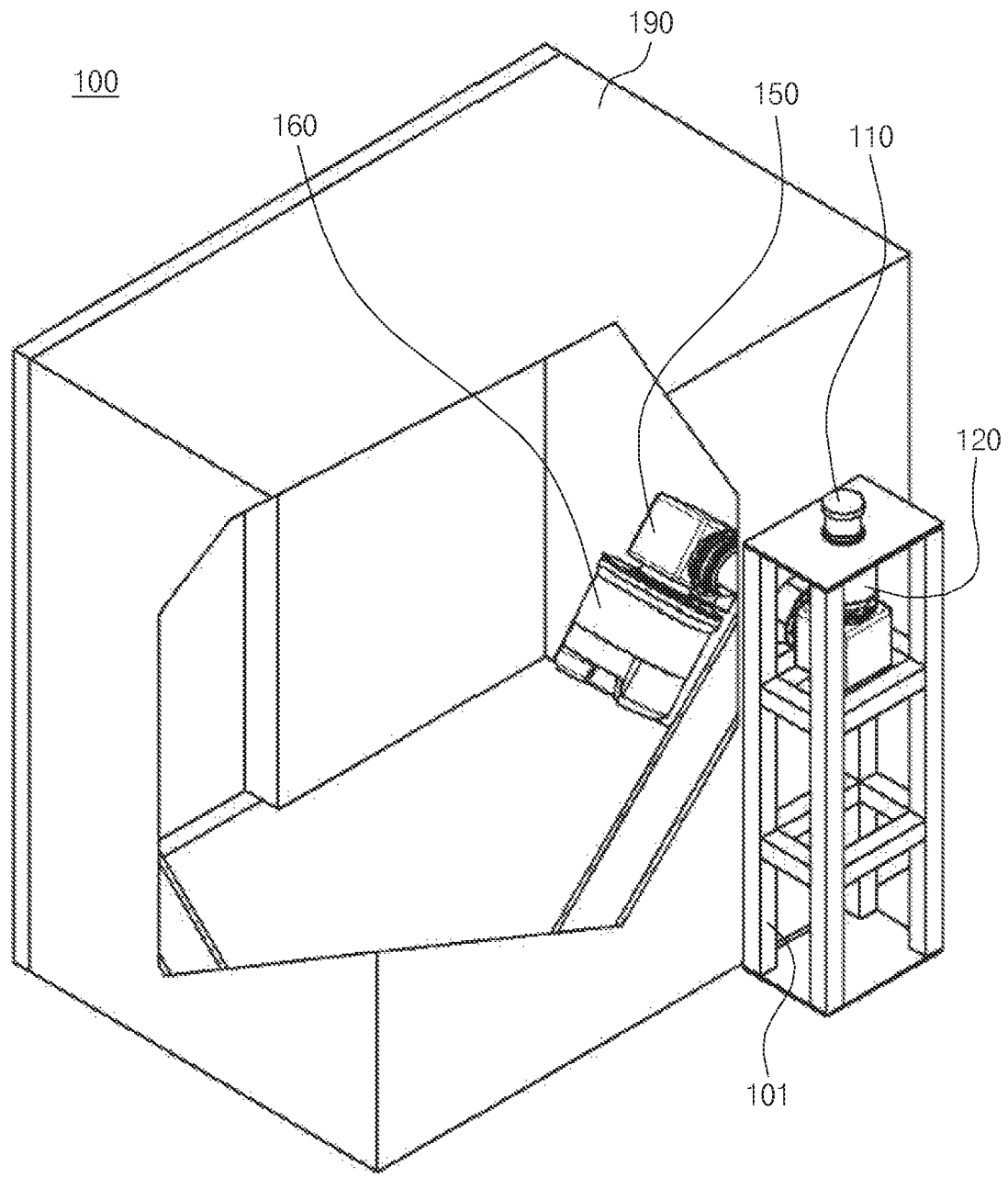
FIG. 1 is a perspective view of a cryocooler SQUID system according to an example embodiment of the present disclosure.

High-priced liquid helium is used to measure an ultra-fine biomagnetic signal using a superconducting quantum interference device (SQUID). Demand for liquid helium is significantly increasing every year with rapid growth of semiconductor industry and medial industry, but supply of a helium gas that is a fossil resource is unstable due to international environment regulation and resource exhaustion. Accordingly, a cooling method using a cryocooler is considered as a cooling method of cooling to a temperature at which a SQUID sensor operates.

However, a cyclic magnetic noise that is several tens to millions of times greater than a biomagnetic signal is generated from a regenerator of a cryocooler to significantly lose and distort an ultra-fine biosignal.

Since the SQUID sensor is cooled based on closed circuit cryocooled thermal conduction, a metal having a high thermal conductivity is mainly used. A thermal noise induced from a surface of the metal greatly changes basic characteristics such as a modulation voltage depth V, a flux voltage conversion factor dv/d, and critical current Ic of the SQUID sensor. Thus, operation stability and sensitivity of a SQUID apparatus are degraded. Moreover, due to degradation in characteristics of the SQUID sensor which is caused by the cyclic magnetic noise and thermal noise, there are many limitations in selecting length, diameter, and material of a thermal rod for cooling the SQUID sensor.

Some study groups applied a superconductive shield to measure a biomagnetic signal under an environment using liquid helium.

In an early-stage cryocooler SQUID system, a cold head chamber and a sensor chamber are integrated into one body to improve heat transfer. The integrated cryocooler SQUID system generates many cyclic magnetic noises.

Size and the number of thermal rods used for thermal conduction between the cold head and the SQUID sensor cannot increase because the thermal noise generated by the metal increases.

In the present disclosure, a superconductive shield using a superconductor (Pb, Nb, etc.) is used for effective thermal conduction from a cryocooler to a SQUID sensor and for shielding a thermal noise of a thermal rod and a thermal shield. The superconductive shield may shield the periphery of the SQUID sensor to eliminate the limitations of length, diameter, and material of a thermal rod. A transferred heat U transferred by the thermal rod is defined as follows: $U=kA/L$. Thus, thermal loss may be compensated by increasing an area A of the thermal rod as a length L of the thermal rod increases. As a result, a cold head of a cryocooler may be magnetically and spatially isolated from the SQUID sensor. The magnetic isolation may further reduce the magnetic noise.

The cold head of the cryocooler isolated from the SQUID sensor may restrict and suppress a cyclic magnetic noise generated from a regenerator by mounting a cold head shield of a cylindrical Permalloy material around the cold head chamber. Thus, an influence provided to a magnetically shielded room (MSR) by the cyclic magnetic noise is minimized. The spatial isolation of the cold head and the sensor chamber may significantly reduce performance degradation of a SQUID apparatus which is a problem of an existing apparatus and is caused by a cyclic magnetic noise. In particular, when a cold head employing the cold head magnetic shield is disposed outside the magnetically shielded room, the magnetic noise is further reduced.

According to an example embodiment of the present disclosure, a SQUID cooling system includes a sensor chamber accommodating a superconductively shielded SQUID sensor and a cold head chamber accommodating a cold head including a cold head magnetic shield of a ferromagnetic material. The cold head includes a first stage cold head (40 K) and a second stage cold head (4 K).

Heat transfer between the two chambers uses a metal rod having a high thermal conductivity from the second stage cold head (4 K) to the SQUID sensor and a superconductive shield. Also when a thermal rod of the metal rod is used, a thermal noise generated from the superconductive shield is significantly reduced.

A metal tube is used from the first stage cold head (40 K) to a 40 K thermal anchor. That is, as the superconductive shield is used, a thermal rod using a plurality of conventional wires may be changed to be rod-shaped or tube-shaped. Thus, thermal transfer efficiency may be improved and the cold head may be disposed outside the magnetically shield room. As a result, a magnetic noise may be reduced. In addition, a ferromagnetic cold head magnetic shield disposed to cover the cold head may further reduce the magnetic noise.

A multi-layered superinsulator is provided between a first thermal shield and a second thermal shield to minimize radiant heat flowing in from the outside. Each superinsulator blocks heat transferred by superinsulator interlayer conduction by using a polyester net.

A SQUID-mounted helmet on which a 4 K thermal anchor, a 40 K thermal anchor, and the SQUID sensor are mounted is disposed inside the sensor chamber accommodating the SQUID sensor. A support rod formed of a material having a low thermal conductivity such as G-10 fixes the 40 K thermal anchor, the 40 K thermal anchor, and the SQUID-mounted helmet to a top plate of the sensor chamber.

A thermal rod is connected to the 4 K thermal anchor and transfers heat to the superconductive shield and the SQUID sensor. A thermal cap is fixed to the 4 K thermal anchor to improve cooling effect of the SQUID sensor mounted inside a helmet and a pick-up coil spaced apart from the SQUID sensor by approximately 30 mm.

As the superconductive shield is used, a conventional slit-type thermal shield may change into a cylindrical thermal shield. Thus, thermal shield efficiency increases.

A cylindrical 40 K thermal shield formed of a metal is connected to the 40 K thermal anchor. A thermal cap is disposed below the SQUID-mounted helmet on which the SQUID sensor is mounted and is molded in the form of a helmet using a copper mesh to be connected to the 40 K thermal shield.

A SQUID sensor control and signal output line usually employs a copper line having a high thermal conductivity mixed with a manganin line having a low thermal conductivity to achieve effective conductive cooling of a superconductive junction of the SQUID sensor and to prevent heat from flowing in from the outside. A printed circuit board (PCB) capable of connecting a lead-in wire to the 4 K thermal anchor is thermally attached. A manganin line is used as a connection box that connects a copper line to an external circuit in a direction of the SQUID sensor.

According to an example embodiment of the present disclosure, a closed circuit cryocooled SQUID MEG apparatus may simultaneously implement chair type advantageous in cognitive measurement and bed type advantageous in patient measurement. To simultaneously implement the two types, an L-shaped first elbow block is mounted at a cold head chamber of a cryocooler mounted outside a magnetically shield room. An L-shaped second elbow block is mounted at a SQUID sensor chamber mounted inside the magnetically shielded room. The first and second elbow blocks are connected by a connection block. The connection block is in the form of a tube, the inside of the connection block is maintained in a vacuum state.

The inside of the connection block connecting the two elbow blocks may displace the sensor chamber at various angles while being maintained at the vacuum state. A rotational motion driver for angle change of the sensor chamber is mounted at the second elbow block attached to an upper end of the sensor chamber. The rotational motion driver may be manipulated using a gear, a handle driving the gear or a motor.

The present disclosure relates to a shield-closed circuit cryocooled SQUID apparatus. The apparatus is characterized in shielding a SQUID sensor with a superconductor and shielding a cold head of a cryocooler with permalloy.

According to an example embodiment of the present disclosure, a thermal noise influence of a thermal transfer medium according to superconductive shielding may be eliminated to release limitation in length, shape, and material of a 4 K thermal rod. The limitation in length of the thermal transfer medium may be released to separate a cold head chamber accommodating a cold head from a sensor chamber accommodating a SQUID sensor. The separated cold head chamber may be mounted outside a magnetically shielded room to further reduce a magnetic noise.

According to an example embodiment of the present disclosure, to reduce an influence on a magnetically shielded room, a cold head may be applied to ferromagnetic shielding by using a material of high magnetic permeability.

According to an example embodiment of the present disclosure, separated two chambers are connected to a connection block including two elbow blocks. The connection block may provide a rotational motion driver capable of changing a position of a chamber accommodating a SQUID sensor.

Example embodiments will now be described more fully with reference to the accompanying drawings, in which some example embodiments are shown. Example embodiments may, however, be embodied in many different forms and should not be construed as being limited to the embodiments set forth herein; rather, these example embodiments are provided so that this disclosure will be thorough and complete, and will fully convey the scope of example embodiments of inventive concepts to those of ordinary skill in the art. In the drawings, the thicknesses of layers and regions are exaggerated for clarity. Like reference characters and/or numerals in the drawings denote like elements, and thus their description may be omitted.

FIG. 1 is a perspective view of a cryocooler SQUID system according to an example embodiment of the present disclosure.

Figure 2:
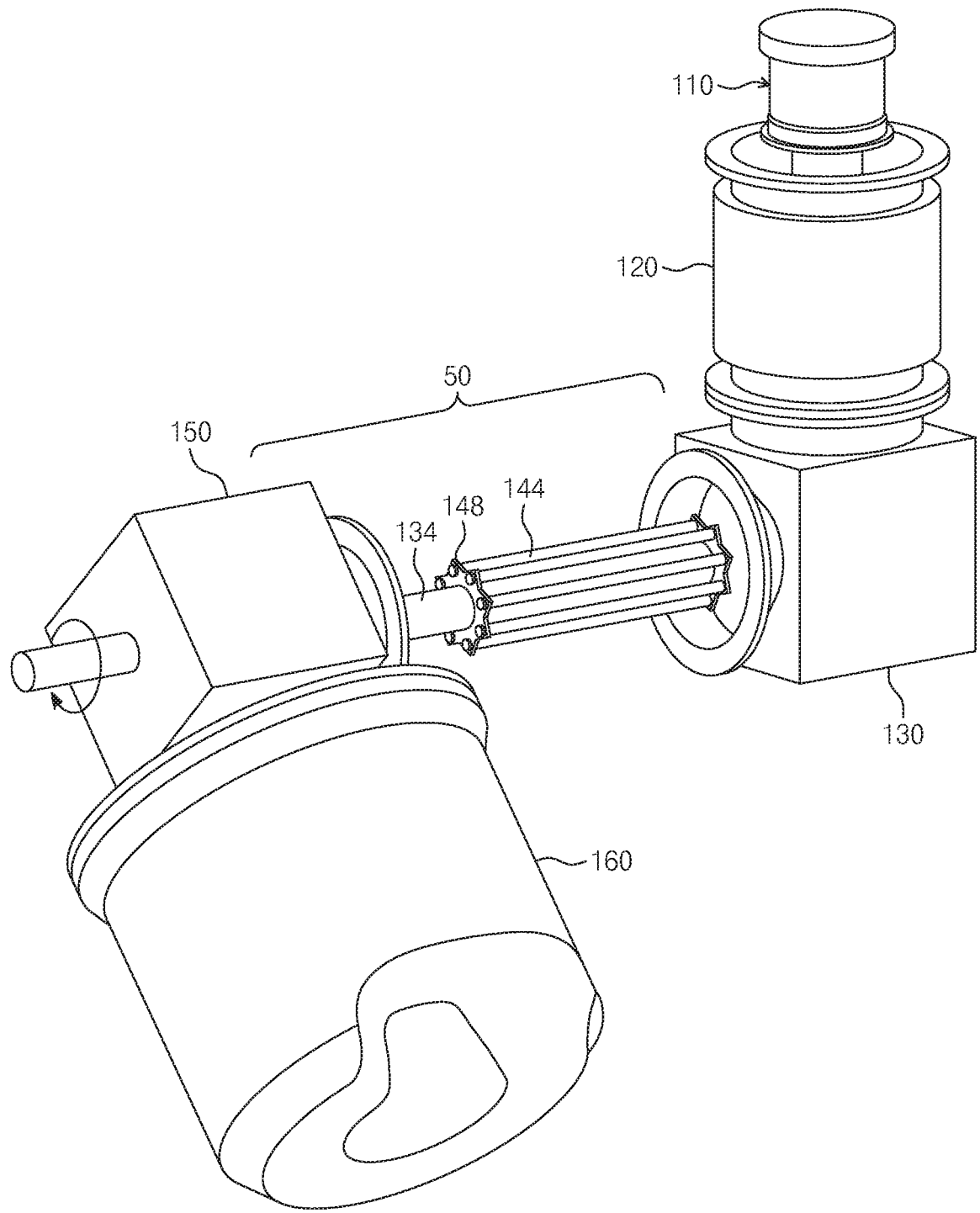
FIG. 2 is a perspective view of the cryocooler SQUID system from which a connection block is removed in FIG. 1.

FIG. 2 is a perspective view of the cryocooler SQUID system from which a connection block is removed in FIG. 1.

Figure 3:
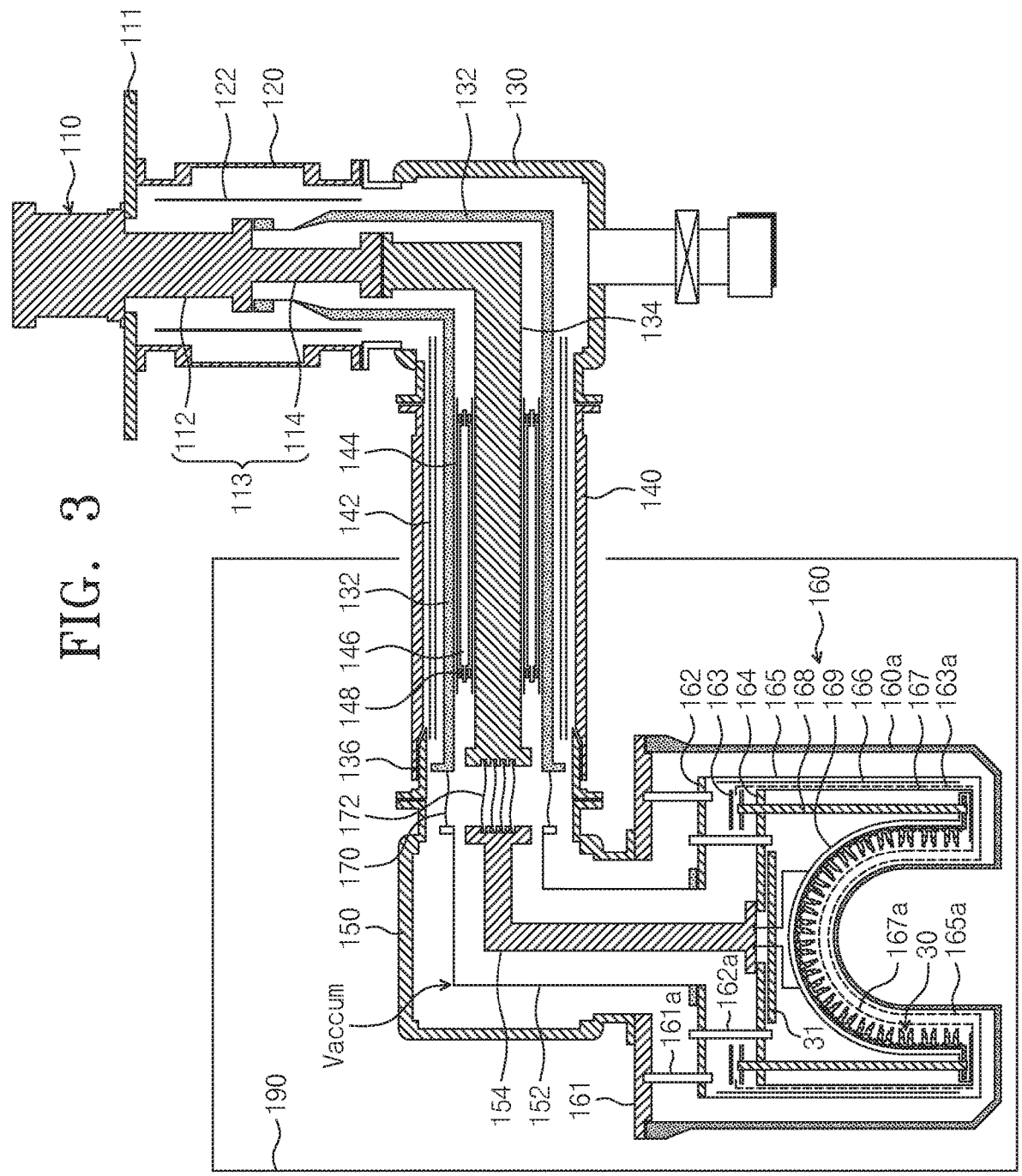
FIG. 3 is a cross-sectional view of the cryocooler SQUID system in FIG. 2.

FIG. 3 is a cross-sectional view of the cryocooler SQUID system in FIG. 2.

Figure 4:
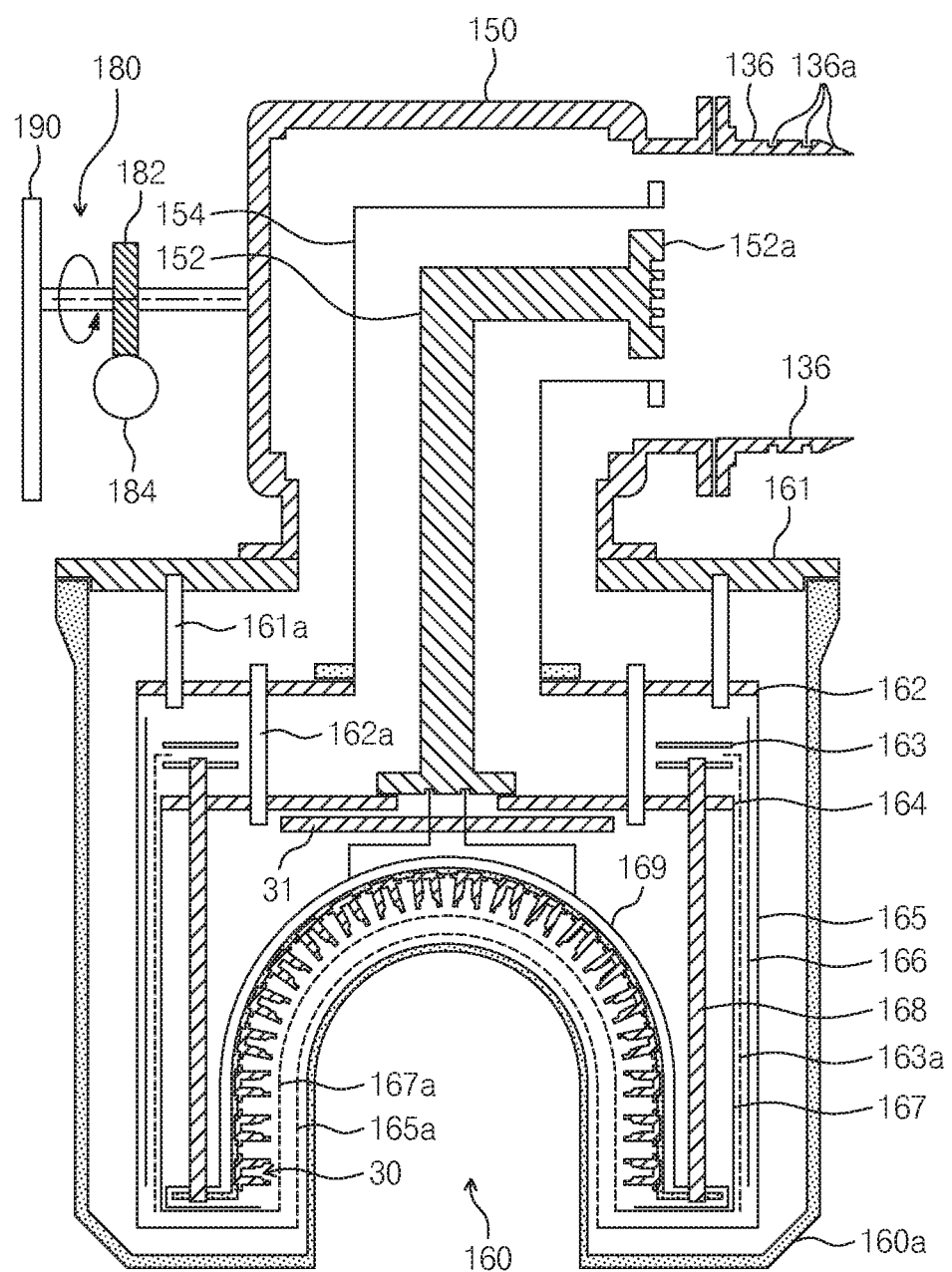
FIG. 4 is an enlarged cross-sectional view of a sensor chamber and a connection block in FIG. 3.

FIG. 4 is an enlarged cross-sectional view of a sensor chamber and a connection block in FIG. 3.

Figure 5:
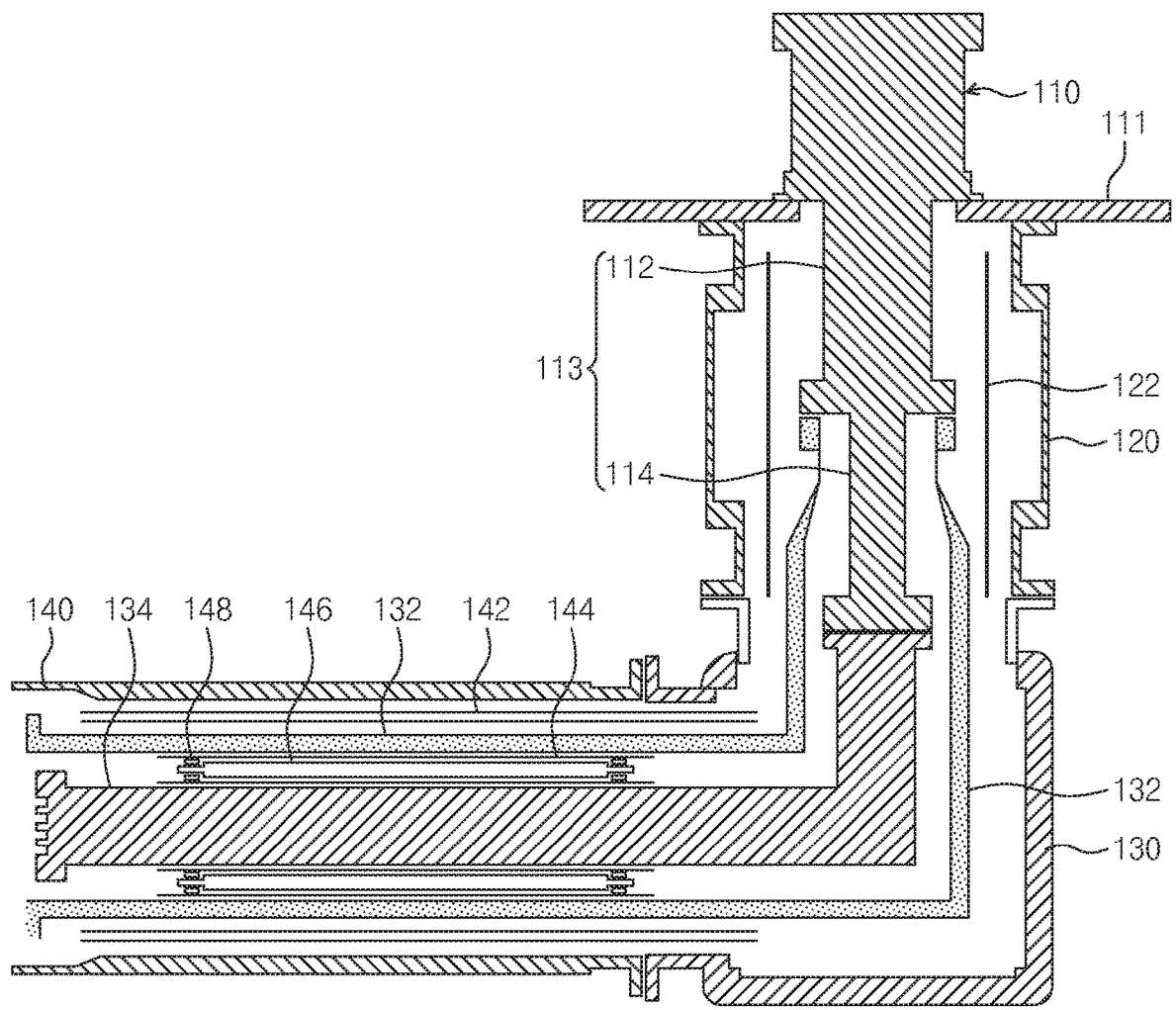
FIG. 5 is an enlarged cross-sectional view of the connection block and a cold head chamber in FIG. 3.

FIG. 5 is an enlarged cross-sectional view of the connection block and a cold head chamber in FIG. 3.

Figure 6:
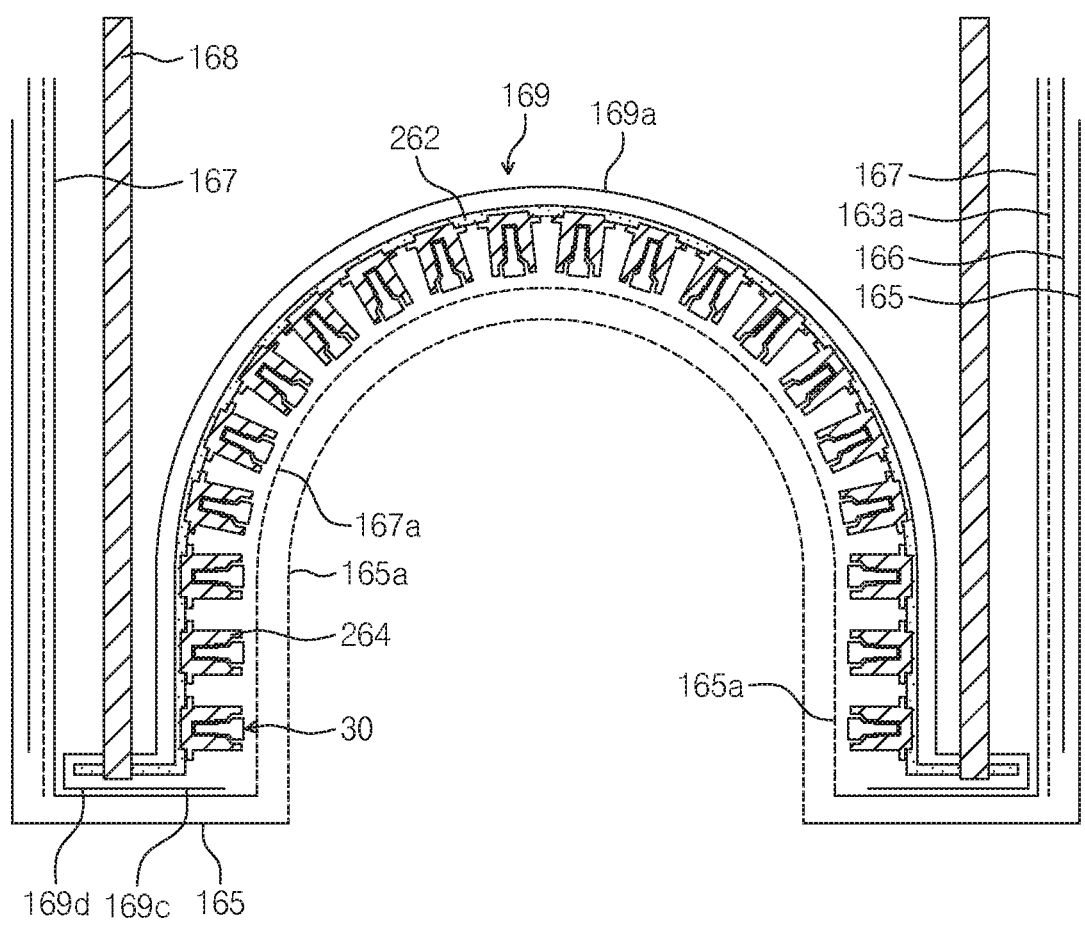
FIG. 6 is an enlarged cross-sectional view of a sensor-mounted helmet in FIG. 3.

FIG. 6 is an enlarged cross-sectional view of a sensor-mounted helmet in FIG. 3.

Figure 7:
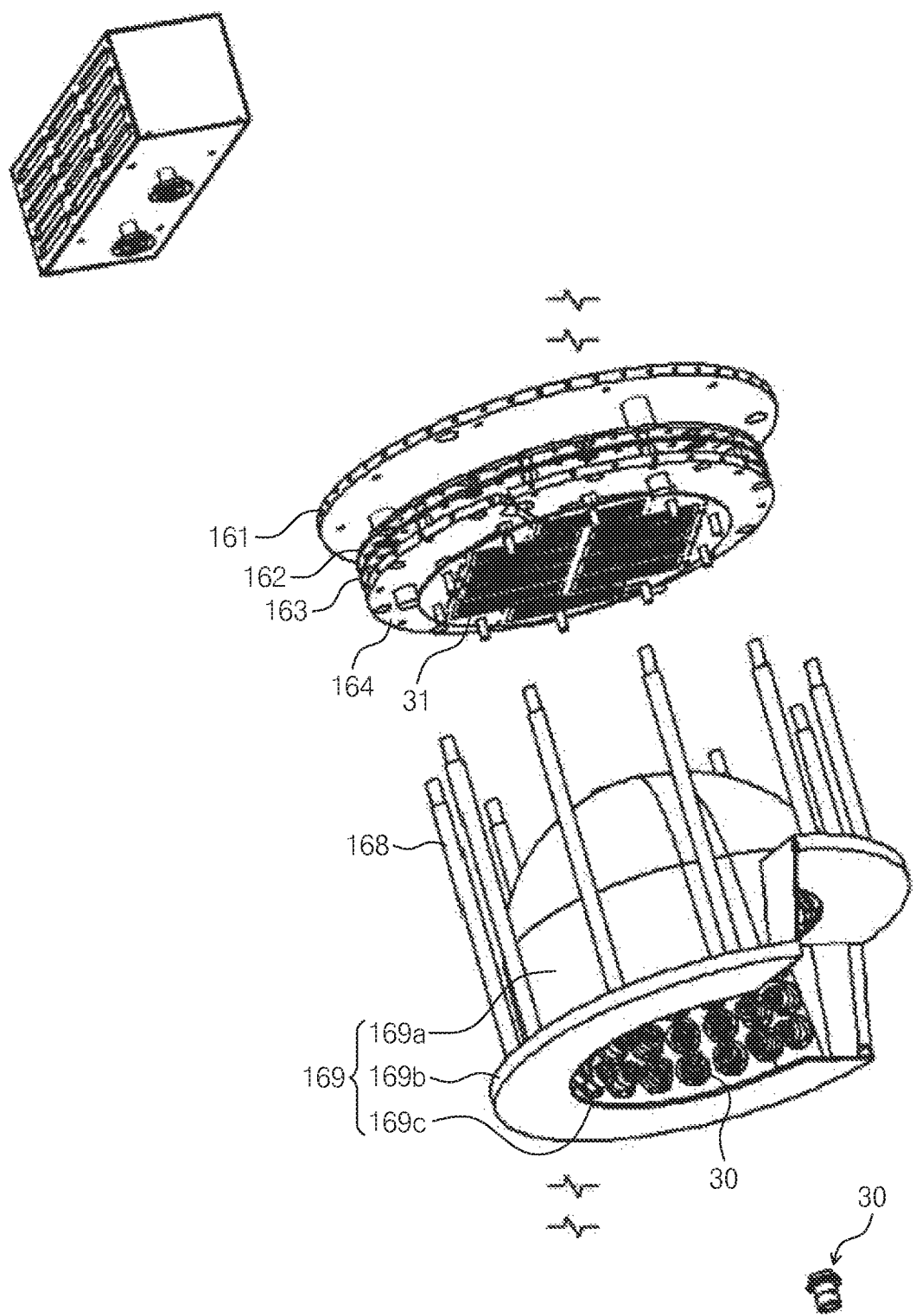
FIG. 7 is a perspective view of a SQUID helmet in FIG. 1.

FIG. 7 is a perspective view of a SQUID helmet in FIG. 1.

Figure 8A:
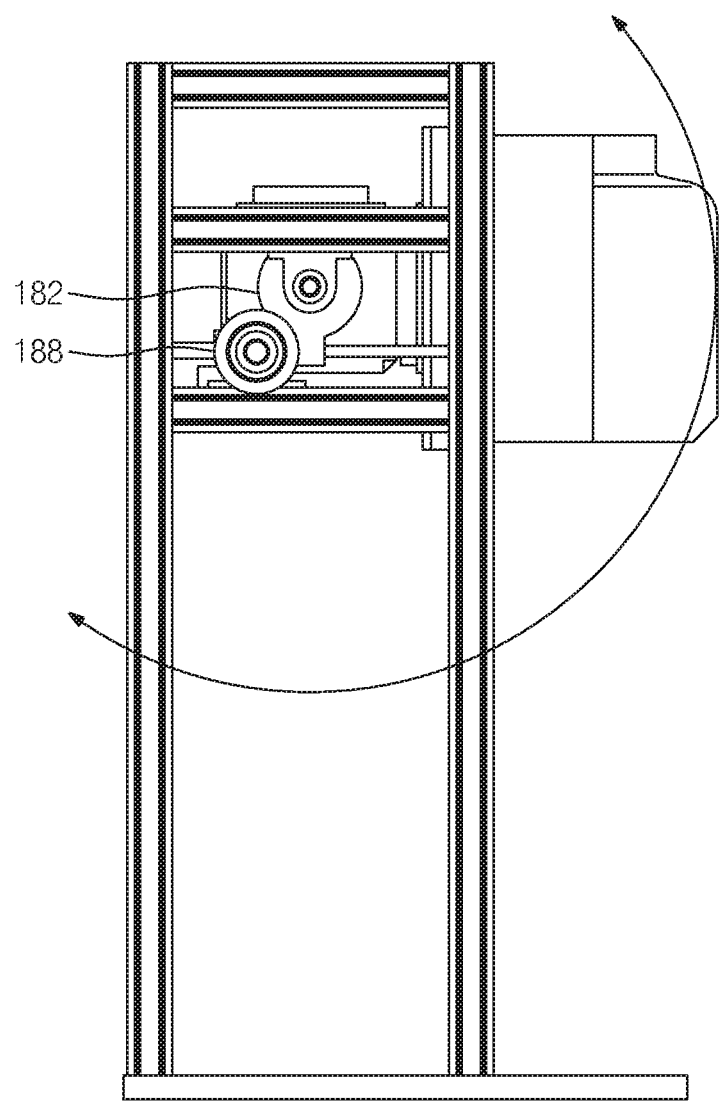
FIGS. 8A and 8B are a top plan view and a side view of a rotatory motion driver in FIG. 1, respectively.
Figure 8B:
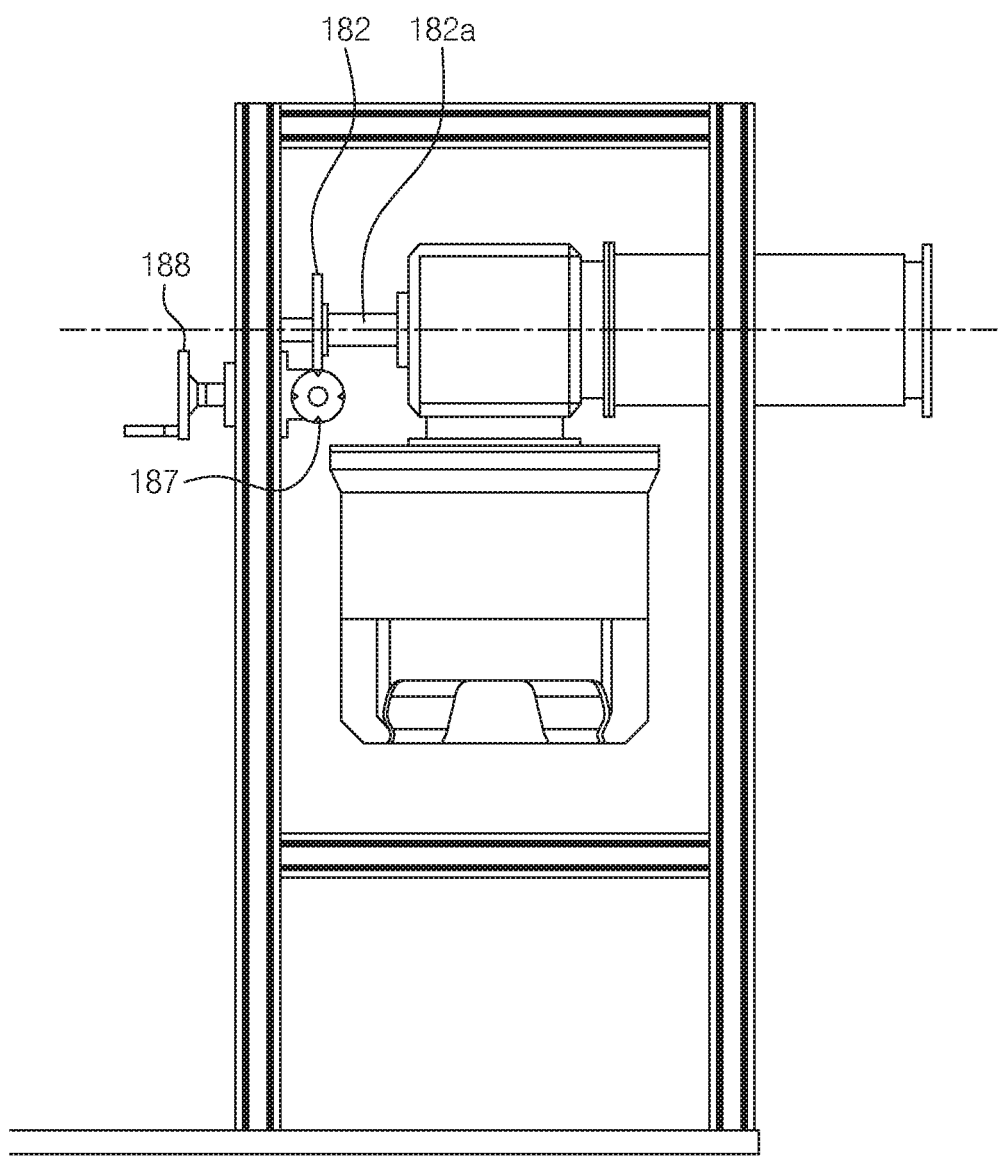

FIGS. 8A and 8B are a top plan view and a side view of a rotatory motion driver in FIG. 1, respectively.

Figure 8C:
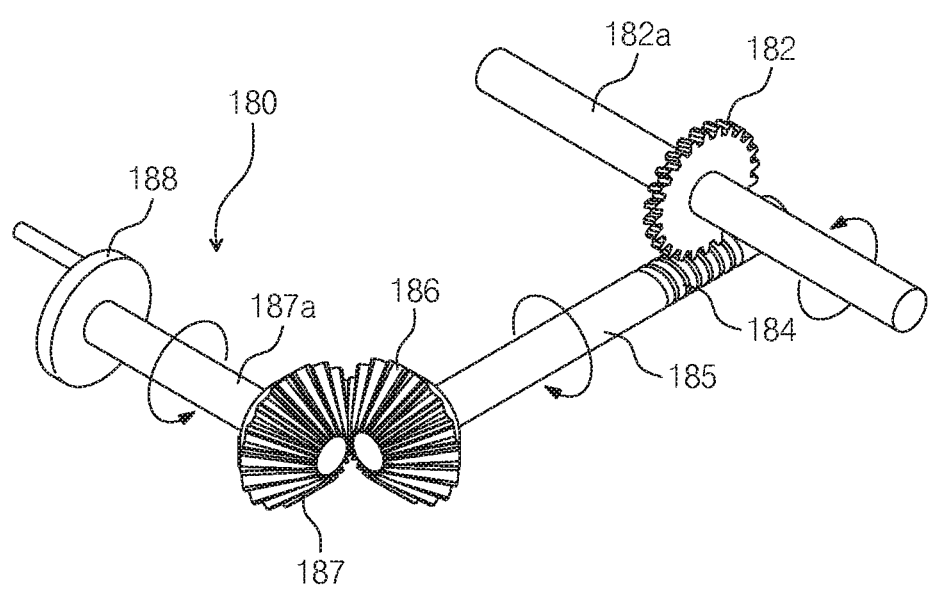
FIG. 8C is a perspective view of the rotational motion driver in FIG. 1.

FIG. 8C is a perspective view of the rotational motion driver in FIG. 1.

Referring to FIGS. 1 through 6, a cryocooler superconducting quantum interference device (SQUID) system 100 includes a cryocooler 110 including a cold head 113, a cold head chamber 120 in which the cold head 113 is disposed, a sensor chamber 160 including a SQUID sensor 30 cooled to a low temperature by the cryocooler 110, and a connection block 50 connecting the cold head 113 with a thermal anchor disposed in the sensor chamber 160 to cool the SQUID sensor 30.

Since a conventional SQUID apparatus is limited in material and area of a thermal rod for heat transfer, a cold head of a cryocooler cannot be separated from a sensor chamber. Specifically, in the case that a rod-shaped thermal rod is used, a SQUID sensor may be inoperable due to a thermal noise. Thus, a plurality of copper wires or a carbon rod is used to suppress the thermal noise. The copper wire or the carbon rod has a limitation in heat transfer. Moreover, cooling efficiency of a cryocooler is significantly reduced according to an inclined angle of the cold head to make it difficult to change a position of the sensor chamber. This is a disadvantage that a cognitive function test mainly conducted in a sitting state and patient measurement conducted in a lying state cannot be performed at the same time.

The cold head chamber 120 accommodating the cold head 113 may be separated from the sensor chamber 160 accommodating the SQUID sensor 30. The spatial separation may result from thermal noise shielding of a superconductive shield disposed around a SQUID magnetometer or a cold head magnetic shield disposed around the cold head 113. Thus, as a rod-shaped or pipe-shaped thermal rod is used, thermal transfer efficiency may be improved to separate the two chambers from each other.

The cold head chamber 120, the connection block 50, and the sensor chamber 160 may be maintained in a vacuum state. To this end, the connection block 50 may include a vacuum port and the vacuum port may be connected to a vacuum pump through bellows. The vacuum state may suppress heat transfer caused by conduction.

A magnetically shielded room 190 may be formed of Mu-metal having a high permeability and aluminum having a high electric conductivity. The sensor chamber 160 may be disposed inside the magnetically shielded room 160. The cryocooler 10 may be disposed outside the magnetically shielded room 190. Thus, an influence of a cyclic magnetic noise generated from the cryocooler 110 may be reduced in the sensor chamber 160.

According to a modified embodiment of the present disclosure, the cold head chamber 120 and the sensor chamber 160 may be disposed inside the magnetically shielded room 190.

According to a modified embodiment of the present disclosure, even when the cold head chamber 120 and the sensor chamber 160 are integrated into one body, superconductive shielding of the SQUID sensor 30 and cold head shielding using the Mu-metal may be applied.

The cryocooler 110 may be a pulse tube cryocooler. The pulse tube cryocooler may employ a closed cycle cooling technique.

The cryocooler 110 may include the cold head 113. The cold head 113 may include a first stage cold head 112 cooled at a first temperature 40 K and a second stage cold head 114 cooled at a second temperature 4 K lower than the first temperature 40 K.

The cold head chamber 120 may be a cylindrical vacuum chamber disposed to cover the first stage cold head 112 and the second stage cold head 114. The cold head chamber 120 may be formed of a metal.

A cold head magnetic shield 122 may be disposed to cover the cold head 113 and may be formed of permalloy. The cold head magnetic shield 112 may be a nickel-iron alloy. The cold head magnetic shield 122 may ferromagnetically shield the cold head 112 using Mu-metal 1 (78% nickel-alloy). The cold head magnetic shield 122 may suppress a cyclic magnetic noise of the cold head 112. The suppression of the cyclic magnetic noise by the cold head magnetic shield 122 may provide use of a cryocooler as cooling means of the SQUID system 100.

The connection block 50 may include a first elbow block 130 connected to the cold held chamber 120, a straight block 140 connected to the first elbow block 130, and a second elbow block 150 connected to the straight block 140.

A first thermal transfer tube 132 may be disposed inside the first elbow block 130 and the straight block 140 and may be elbow-shaped. A first thermal transfer rod 134 may be disposed inside the first thermal transfer tube 132 and may be L-shaped. A second thermal transfer tube 152 may be disposed inside the second elbow block 150 and may be in the form of an elbow. A second thermal transfer rod 154 may be disposed inside the second thermal transfer tube 152 and may be L-shaped.

The first elbow block 130 may be combined with a flange formed on a bottom surface of the cold head chamber 120. The first elbow block 130 may be a rectangular parallelepiped chamber formed of a metal. Flanges may be disposed on both surfaces parallel to each other of the first elbow block 130.

The straight block 140 may be disposed through a wall of the magnetically shielded room 190. The straight block 140 may be formed of a metal and have a cylindrical shape. Opposite ends of the straight block 140 may be combined with the first and second elbow blocks 130 and 150 through the flange, respectively.

The second elbow block 150 may be connected to the sensor chamber 160 through the flange. The second elbow chamber 150 may be a rectangular parallelepiped chamber formed of a metal. Flanges may be disposed at both surfaces vertical to each other of the second elbow block 150.

The thermal transfer tubes 132 and 152 may be tube-shaped, may be disposed inside the connection block 50, and may connect the first stage cold head 112 to the first thermal anchor 162 disposed in the sensor chamber 160. The thermal transfer tubes 132 and 152 may include the first thermal transfer tube 132 and the second thermal transfer tube 152. As the tube-shaped thermal transfer tubes 132 and 152 improve thermal transfer capability, a distance between the sensor chamber 160 and the cold head chamber 120 may be maintained by 1 meter or longer. The thermal transfer tubes 132 and 152 and the first thermal anchor 162 may be maintained at a temperature of 40 Kelvin (K).

The thermal transfer rods 134 and 154 may be disposed inside the thermal transfer tubes 132 and 152, respectively and connect the second stage cold head 114 to the second thermal anchor 164 disposed in the sensor chamber 160. The thermal transfer rods 134 and 154 may include the first thermal transfer rod 134 and the second thermal transfer rod 154. The thermal transfer rods 134 and 154 and the second thermal anchor 164 may be maintained at a temperature of 4 K.

The first thermal transfer tube 132 may be an L-shape cylinder. One end of the first thermal transfer tube 132 may be thermally connected to the first stage cold head 112. The first thermal transfer tube 132 may be disposed inside the first elbow block 130 and the straight block 140. A material of the first thermal transfer tube 132 may be copper.

The first thermal transfer rod 134 may be an L-shaped pillar. The first thermal transfer rod 134 may be thermally connected to the second stage cold head 114. The first thermal transfer rod 134 may be disposed inside the first thermal transfer tube 132. A material of the first thermal transfer rod 134 may be copper.

The second thermal transfer tube 152 may be an L-shaped cylinder. One end of the second thermal transfer tube 152 may be thermally connected to the first thermal anchor 162. The second thermal transfer tube 152 may be disposed inside the second elbow block 150. A material of the second thermal transfer tube 152 may be copper.

The second thermal transfer rod 154 may be an L-shaped pillar. The second thermal transfer rod 154 may be thermally connected to the second thermal anchor 164. The second thermal transfer rod 154 may be disposed inside the second thermal transfer tube 152. A material of the second thermal transfer rod 154 may be copper.

The first thermal transfer tube 132 and the second thermal transfer tube 152 may be connected by a braided copper wire 170. The first thermal transfer rod 134 and the second thermal transfer rod 154 may be connected by a braided copper wire 172. When the second sensor chamber 160 rotates, the braided copper wires 170 and 172 may be twisted according to the rotation of the second sensor chamber 160 because they have flexibility. The braided copper wires 170 and 172 may reduce vibration transmission caused by a high-voltage pulse (~2 Hz) of the cryocooler 110.

A rotation flange 136 may be disposed at a portion where the first thermal transfer tube 132 and the second thermal transfer tube 152 are connected and may provide a rotational motion to the second elbow block 150 and the sensor chamber 160. More specifically, one end of the rotation flange 136 may be in the form of a tapered tube inserted into an inner side of the straight block 140. A groove 136a may be formed on a tapered and tube-shaped surface to maintain a vacuum state. An O-ring inserted into the groove 136a may maintain the vacuum state. The rotational flange 136 may be connected to the second elbow block 150. As the second elbow block 150 rotates, the rotation flange 136 may rotate together with the second elbow block 150. The straight block 140 connected to the rotation flange 136 may be fixed without rotating.

An internal adiabatic layer 144 may be disposed between the thermal transfer rod 132 and the thermal transfer tube 134 to reduce radiant heat. In addition, an external adiabatic layer 142 may be disposed between the thermal transfer tube 134 and the straight block 140. The internal adiabatic layer 144 and the external adiabatic layer 142 may include a multi-layered superinsulator to minimize radiant heat flowing in from the outside. The superinsulator may block thermal transfer caused by interlayer conduction by using a polyester net.

Space maintaining portions 146 and 148 may be formed of an adiabatic material and may be disposed between the thermal transfer rod 132 and the thermal transfer tube 134 to be maintained by a fixed distance. Specifically, the space maintaining portions 146 and 148 may be disposed inside the straight block 140 to be disposed between the first thermal transfer rod 134 and the first thermal transfer tube 132. The space maintaining portions 146 and 148 may be formed of a glass-fiber-reinforced plastic (GFRP).

The space maintaining portions 146 and 148 may include a pair of star-shaped spacers 148 inserted into opposite ends of a straight portion of the thermal transfer rod and a plurality of rod-shaped spacer support 146 connecting a pair of spacers to each other. The spacer 148 may have a star shape to minimize a contact area with the thermal transfer rod. In addition, the spacer 148 may have a star shape to minimize a contact area with the thermal transfer tube 134. The spacer support 146 may be inserted between the rod-shaped spacers 148 spaced apart from each other to maintain a fixed distance therebetween.

A bottom surface of a body of the sensor chamber 160 may include a dent portion. A magnetoencephalography (MEG) signal may be measured while a subject's head is inserted into the dent portion. The sensor chamber 160 may be aligned almost vertically from the ground to measure the MEG signal while the subject sits down. Alternatively, the sensor chamber 160 may be aligned parallel to the ground to measure the MEG signal while the subject sits down. The rotational motion driver 180 may be provided for rotation of the sensor 160.

The rotational motion driver 180 may provide position change of the sensor chamber 160 to measure an MEG signal according to a subject's posture. The rotational motion driver 180 may rotate a central axis of the sensor chamber 160 at an angle between directions vertical and horizontal to the ground.

The rotational motion driver 180 may provide a rotational motion to the second elbow block 150. Since the second elbow block 150 is fixedly coupled to the sensor chamber 160, the sensor chamber 160 may rotate as the second elbow block 150 rotates.

The rotational motion driver 180 may include a worm gear rotation shaft 182a connected to the second elbow block 150 and horizontal to the ground, a worm gear 182 disposed at the work gear rotation shaft 182a, a worm 184 gearing with the worm gear 182, a worm rotation shaft 185 where the worm 184 is formed, a first bevel gear 186 disposed at the worm rotation shaft 185, a second bevel gear 187 gearing with the first bevel gear 186, and a bevel gear rotation shaft 187a combined with the second bevel gear 187. The bevel gear rotation shaft 197a may be connected to a handle 188 or a motor.

As the bevel gear rotation shaft 187a rotates, the first bevel gear 186 and the second bevel gear 187 may rotate. As the first bevel gear 187 rotates, the worm rotation shaft 185 and the worm 184 may rotate. As the worm rotates, the worm gear 182 rotates. As the worm gear 182 rotates, the sensor chamber 160 may rotate.

The flange of the second elbow block 150 may be combined with the periphery of a through-hole formed in the center of a top plate 161 of the sensor chamber 160.

The sensor chamber 160 may the top plate 161 and a sensor chamber body 160a having an empty space formed therein. The sensor chamber 160 includes a first thermal anchor 162, a second thermal anchor 164, a first thermal shield 165, and a second thermal shield 167.

The first thermal anchor 162 may be disposed in the sensor chamber 160 and may be in the form of a washer connected to the thermal transfer tube 154. A material of the first thermal anchor 162 may be copper. The first thermal anchor 162 may be cooled to a temperature of 40 K.

The second thermal anchor 164 may be disposed below the first thermal anchor 162 inside the sensor chamber 160 and may be in the form of a washer connected to the thermal transfer rod 152. A material of the second thermal anchor 164 may be copper. The second thermal anchor 164 may be cooled to a temperature of 4 K.

The first thermal shield 165 may be connected to the first thermal anchor 162 and may be in the form of a cylinder extending in a central axis direction of the sensor chamber 160. A material of the first thermal shield 165 may be copper or aluminum. The first thermal shield 165 may be maintained at a temperature of 40 K.

The second thermal shield 167 may be disposed inside the first thermal shield 165, may be connected to the second thermal anchor 164, and may be in the form of a cylinder extending in the central axis direction of the second chamber 160. A material of the second thermal shield 167 may be copper or aluminum. The second thermal shield 167 may be maintained at a temperature of 4 K.

A pair of auxiliary thermal anchors 163 may be disposed between the first thermal anchor 162 and the second thermal anchor 164. The auxiliary thermal anchors 163 may be in the form of a pair of washers. The pair of washers may be combined to be in contact with each other. An auxiliary thermal transfer portion 163a may be inserted between the auxiliary thermal anchors 163 to extend in the central axis direction of the sensor chamber 160 and may be formed of a copper mesh. The auxiliary thermal anchors 163 may be cooled through the second thermal anchor 164 and a sensor chamber thermal transfer rod 168. Thus, the auxiliary thermal anchors 163 and the auxiliary thermal transfer portion 163a may be cooled to a temperature of 4 K.

The chamber thermal transfer rod 168 may be in thermal contact with the second thermal anchor 164, the auxiliary thermal anchor 163a, and a superconductive shield. The chamber thermal transfer rod 168 may be in the form of a pillar and may be formed of copper. One end of the chamber thermal transfer rod 168 may be fixed to the second thermal anchor 164, and the other end thereof may be fixed to a SQUID sensor-mounted helmet 262.

A first support pillar 161a may fix the top plate 161 and the first thermal anchor 162 to each other, and a second support pillar 162a may fix the first thermal anchor 162 and the second thermal anchor 164 to each other. The first support pillar 161a and the second support pillar 162a may each be a G-10 epoxy rod having a low thermal conductivity.

A printed circuit board (PCB) block 31 may be disposed on a bottom surface of the second thermal anchor 164. The PCB block 31 may receive a signal of the SQUID sensor 30 and may provide a signal to the SQUID sensor 30.

A superconductive shield 169 may be disposed around the SQUID sensor 30 and may be formed of a superconductor to remove an external noise. The superconductor may be lead (Pb) or niobium (Nb). The superconductive shield 169 may be cooled to a temperature of 4 K. To this end, a plurality of grooves may be formed at one end of the second thermal transfer rod 154. The groove of the second thermal transfer rod 154 and the superconductive shield 169 may be connected by a plurality of cooper braided wires. The superconductive shield 169 may have a helmet shape. The superconductive shield 169 may include a hemispherical superconductive helmet body 169a, an outer brim 169b extending outwardly from a bottom surface of the superconductive helmet body 169a, and an inner brim 169c extending inwardly from the bottom surface of the superconductive helmet body 169a. The inner brim 169c may increase an MEG signal around an ear.

The SQUID sensor-mounted helmet 262 may be disposed on the dent portion at a lower portion of the sensor chamber 160. The SQUID sensor-mounted helmet 262 may be disposed inside the sensor chamber 160 maintained in a vacuum state. A plurality of SQUID sensors may be disposed at the SQUID sensor-mounted helmet 262. The SQUID sensor-mounted helmet 262 may be disposed inside the superconductive shield 169. The SQUID sensor-mounted helmet 262 may be formed of G10 epoxy.

The SQUID sensor 30 may be a magnetometer or a gradiometer. The SQUID sensor 30 may include a SQUID and a pick-up coil. The pick-up coil may be a magnetometer or a gradiometer. The SQUID may be a double-relaxation oscillation SQUID (DROS).

A first thermal cap 165a may be cooled to a temperature of 40 K, may be disposed to cover the SQUID sensor 30, may be molded in the form of a helmet, and may be formed of a copper mesh. The first thermal cap 165a may be in thermal contact with the first thermal shield at a bottom surface of the first thermal shield 165.

A second thermal cap 167a may be cooled to a temperature of 4 K, may be disposed between the first thermal cap 165a and the SQUID sensor-mounted helmet 262, may be molded in the form of a helmet, and may be formed of a copper mesh. The second thermal cap 167a may be in thermal contact with the second thermal shield 167 at a bottom surface of the second thermal shield 167.

Figure 9:
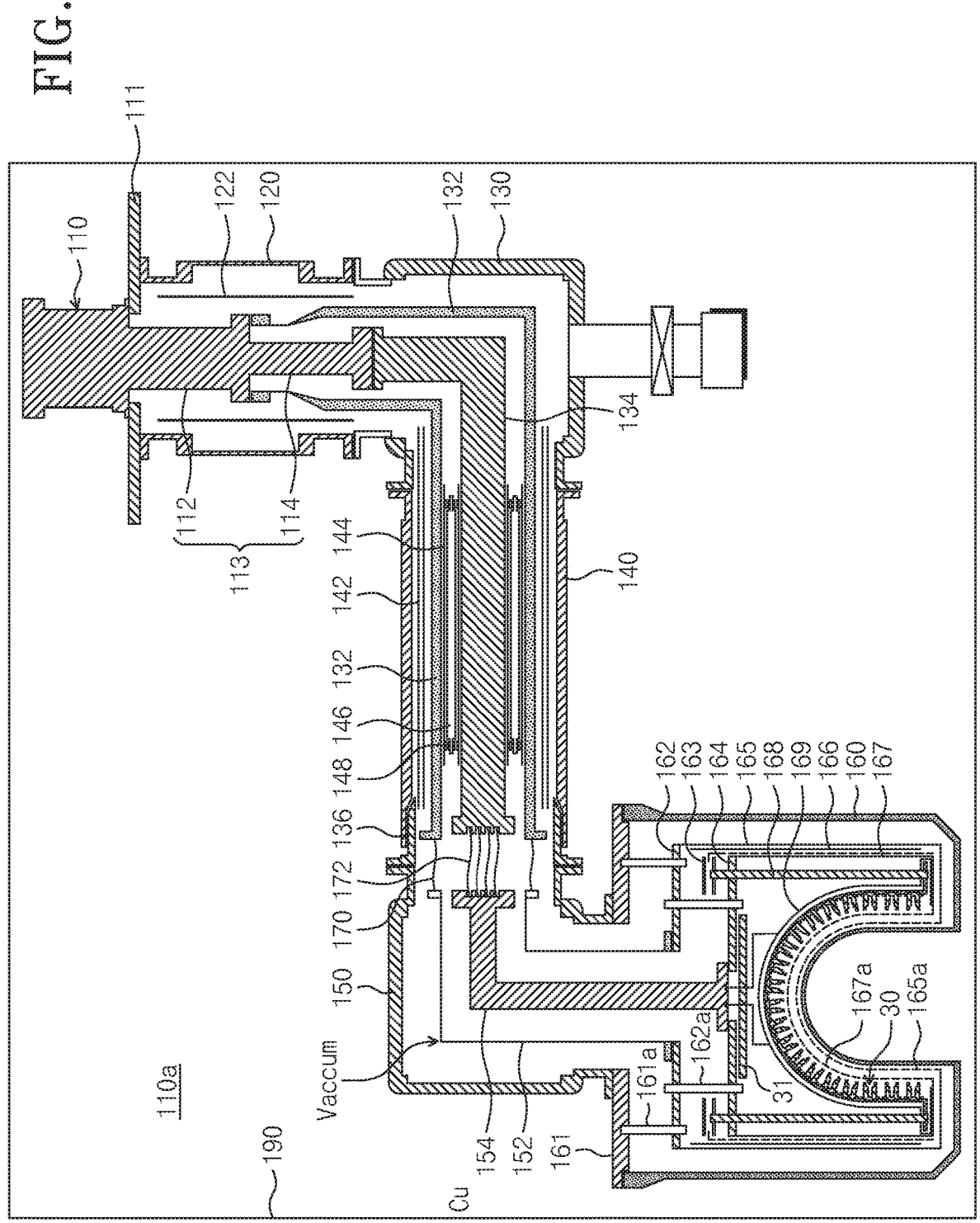
FIG. 9 is a cross-sectional view of a cryocooled SQUID system according to another example embodiment of the present disclosure.

FIG. 9 is a cross-sectional view of a cryocooled SQUID system according to another example embodiment of the present disclosure. In FIG. 9, the same components or parts as those shown in FIGS. 1 to 8 are designated with the same numerals and their explanations will be omitted.

Referring to FIG. 9, a superconducting quantum interference device (SQUID) system 100a includes a cryocooler 110 including a cold head, a cold head chamber 120 in which the cold head 113 is disposed, a sensor chamber 160 including a SQUID sensor 30 cooled to a low temperature by the cryocooler 110. The cold head chamber 120 accommodating the cold head is separated from the sensor chamber 160 accommodating the SQUID sensor 30. The cold head chamber 120 and the sensor chamber 160 may be disposed inside a magnetically shielded room 190.

A cold head magnetic shield 122 may be disposed to cover the cold head. The cold head magnetic shield 122 may be permalloy. The cold head magnetic shield 122 may be Mu-metal of a nickel-iron alloy.

A superconductive shield 169 may be disposed around the SQUID sensor 30 and may be formed of a superconductor.

Figure 10:
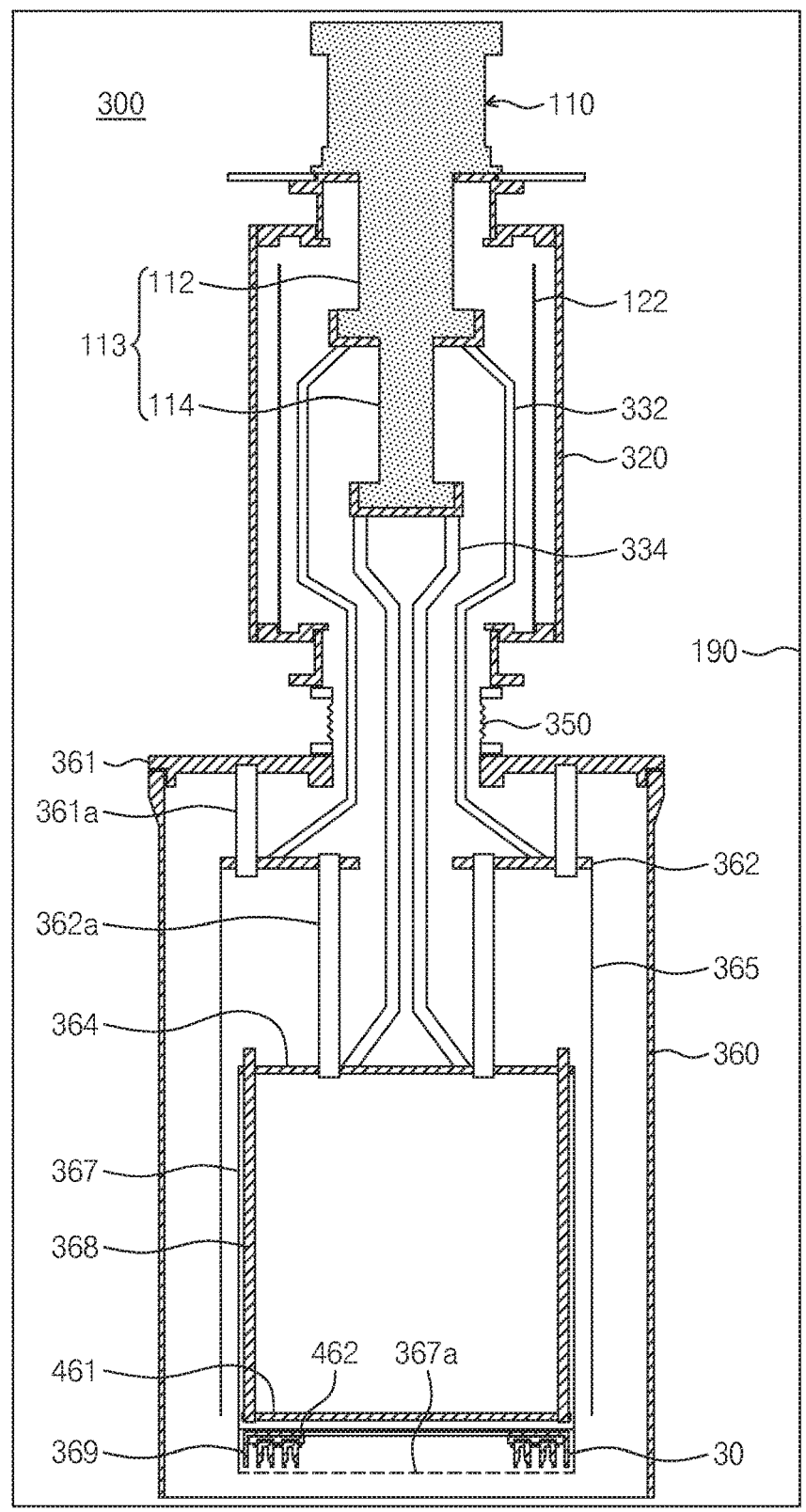
FIG. 10 is a cross-sectional view of a cryocooled SQUID system according to another example embodiment of the present disclosure.

FIG. 10 is a cross-sectional view of a cryocooled SQUID system according to another example embodiment of the present disclosure.

Figure 11:
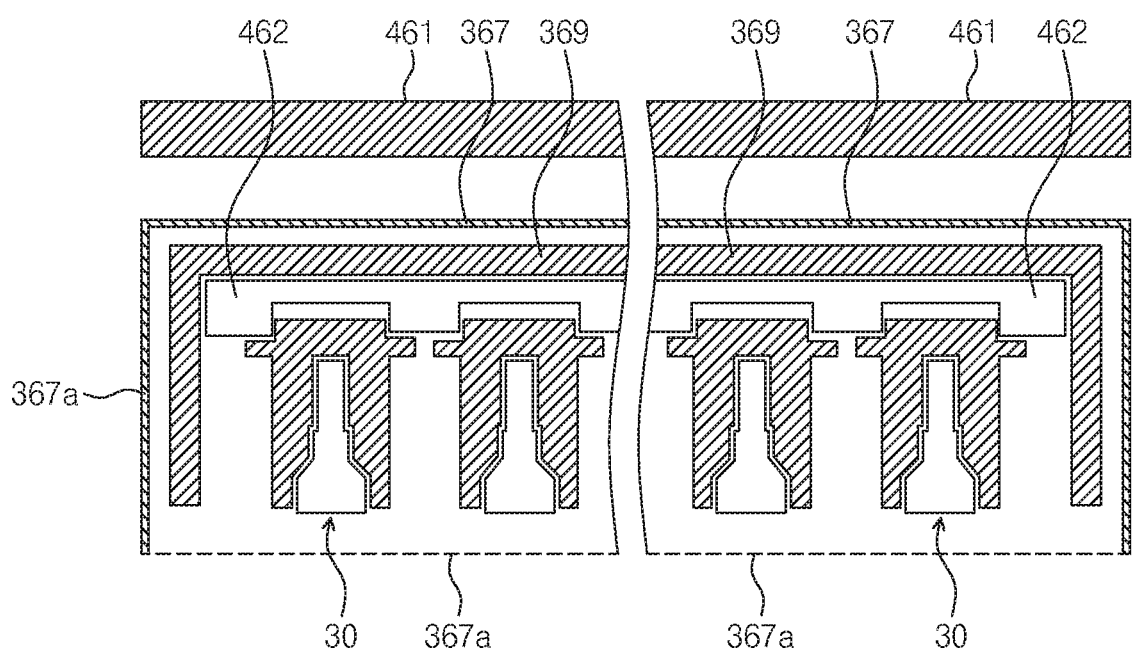
FIG. 11 is an enlarged cross-sectional view showing the periphery of a SQUID magnetometer in FIG. 10.

FIG. 11 is an enlarged cross-sectional view showing the periphery of a SQUID magnetometer in FIG. 10.

Referring to FIGS. 10 and 11, a cryocooler superconducting quantum interference device (SQUID) system 300 includes a cryocooler 110 including a cold head, a cold head chamber 320 in which the cold head 113 is disposed, a sensor chamber 360 including a SQUID sensor 30 cooled to a low temperature by the cryocooler 110, and a connection block 350 connecting the cold head 113 to a thermal anchor disposed in the sensor chamber 360 to cool the SQUID sensor 30 in the sensor chamber 360. The cold head chamber 320 and the sensor chamber 360 are disposed inside a magnetic shielded room 190.

The cryocooler 110 may include a cold head 113. The cold head 113 may include a first stage cold head 112 cooled to a first temperature (40 K) and a second cold head 114 cooled to a second temperature (4 K) lower than the first temperature.

The cold head chamber 320 may be a cylindrical vacuum chamber disposed to cover the first stage cold head 112 and the second stage cold head 114. The cold head chamber 320 may be formed of a metal.

A cold head magnetic shield 122 may be disposed to cover the cold head 113 and may be formed of permalloy. The cold head magnetic shield 122 may be a nick-iron alloy. The cold head magnetic shield 122 may be in the form of a cylinder to ferromagnetically shield the cold head 113 using Mu-metal 1 (78% nickel alloy). The cold head magnetic shield 122 may suppress a cyclic magnetic noise of the cold head 113. The suppression of the cyclic magnetic noise by the cold head magnetic shield 122 may provide use of a cryocooler as cooling means of the SQUID system 300.

The connection block 350 may be bellows to reduce a vibration.

Thermal transfer portions 332 and 334 may thermally contact the cold head 113 and thermal anchors 362 and 364 with each other. The thermal transfer portions 332 and 334 may be flexible braided copper wires. A length of the flexible braided copper wire may be approximately 1 meter (m). Specifically, a length of the flexible braided copper wire may be between 500 to 2000 millimeters (mm). The thermal transfer portions 332 and 334 may include a first thermal transfer portion 332 and a second thermal transfer portion 334. Each of the first thermal transfer portion 332 and the second thermal transfer portion 334 may be formed of a flexible braided copper wire.

The first stage cold head 112 may be connected to the first thermal anchor 362 of 40 K by the first thermal transfer portion 332, and the second stage cold head 114 may be connected to the second thermal anchor 364 of 4 K by the second thermal transfer portion 334.

The sensor chamber 360 may include a top plate 361 and a sensor chamber body having an empty space formed therein. The sensor chamber 360 may include a first thermal anchor 362, a second thermal anchor 364, a first thermal shield 365, and a second thermal shield 367.

The first thermal anchor 362 may be disposed in the sensor chamber 360, may be connected to the first thermal transfer portion 332, and may be in the form of a washer. A material of the first thermal anchor 362 may be copper. The first thermal anchor 362 may be cooled to a temperature of 40 K.

The second thermal anchor 364 may be disposed below the first thermal anchor 362 inside the sensor chamber 360, may be connected to the second thermal transfer portion 334, and may be in the form of a washer. A material of the second thermal anchor 364 may be copper. The second thermal anchor 364 may be cooled to a temperature of 4 K.

The first thermal shield 365 may be connected to the first thermal anchor 362 and may be in the form of a cylinder extending in a central axis direction of the sensor chamber 360. A material of the first thermal shield 365 may be copper or aluminum. The first thermal shield 365 may be maintained at a temperature of 40 K.

The second thermal shield 367 may be disposed inside the first thermal shield 365, may be connected to the second thermal anchor 364, and may be in the form of a cylinder extending in the central axis direction of the second chamber 360. A material of the second thermal shield 367 may be copper or aluminum. The second thermal shield 367 may be maintained at a temperature of 4 K.

A pair of auxiliary thermal anchors (not shown) may be disposed between the first thermal anchor 362 and the second thermal anchor 364. The auxiliary thermal anchors may be in the form of a pair of washers. The pair of washers may be combined to be in contact with each other. An auxiliary thermal transfer portion may be inserted between the auxiliary thermal anchors to extend in the central axis direction of the sensor chamber 360 and may be formed of a copper mesh. The auxiliary thermal anchors may be cooled through the second thermal anchor 364 and a sensor chamber thermal transfer rod 368. Thus, the auxiliary thermal anchors and the auxiliary thermal transfer portion may be cooled to a temperature of 4 K.

The chamber thermal transfer rod 368 may be in thermal contact with a sensor cooling plate 461. The chamber thermal transfer rod 368 may be in the form of a pillar and may be formed of copper. One end of the chamber thermal transfer rod 368 may be fixed to the second thermal anchor 364, and the other end thereof may be fixed to the sensor cooling plate 461.

A first support pillar 361a may fix the top plate 361 and the first thermal anchor 362 to each other, and a second support pillar 362a may fix the first thermal anchor 362 and the second thermal anchor 364 to each other. The first support pillar 361a and the second support pillar 362a may each be a G-10 epoxy rod having a low thermal conductivity.

A printed circuit board (PCB) block may be disposed on a bottom surface of the second thermal anchor 364. The PCB block may receive a signal of the SQUID sensor 30 and may provide a signal to the SQUID sensor 30.

The sensor cooling plate 461 may be cooled to a temperature of 4 K by the chamber thermal transfer rod 368. The sensor cooling plate 461 may be a copper or aluminum plate.

A thermal cap 367 may be disposed below the sensor cooling plate 461. The thermal cap 367 may be disposed to cover a bottom surface and a top surface of a SQUID sensor mounting plate. A top surface of the thermal cap 367 may be in the form of a plate, and a bottom surface thereof may be formed of a copper mesh.

A superconductive shield 369 may be disposed around the SQUID sensor 30 to remove an external noise and may be formed of a superconductor. The superconductive shield 369 may be in the form of a disc. The superconductor may be lead (Pb) or niobium (Nb). The superconductive shield 369 may be in contact with the thermal cap 367 and in thermal contact with the sensor cooling plate 461 to be cooled to a temperature of 4 K.

The SQUID sensor mounting plate 462 may be disposed adjacent to a bottom surface of the sensor chamber 360. The SQUID sensor mounting plate 462 may be disposed inside the sensor chamber 360 maintained in a vacuum state. A plurality of SQUID sensors may be disposed at the SQUID sensor mounting plate 462. The SQUID sensor mounting plate 462 may be formed of G10 epoxy.

The SQUID sensor 30 may be a magnetometer or a gradiometer. The SQUID sensor 30 may include a SQUID and a pick-up coil. The pick-up coil may be a magnetometer or a gradiometer. The SQUID may be a double-relaxation oscillation SQUID (DROS).

Figure 12:
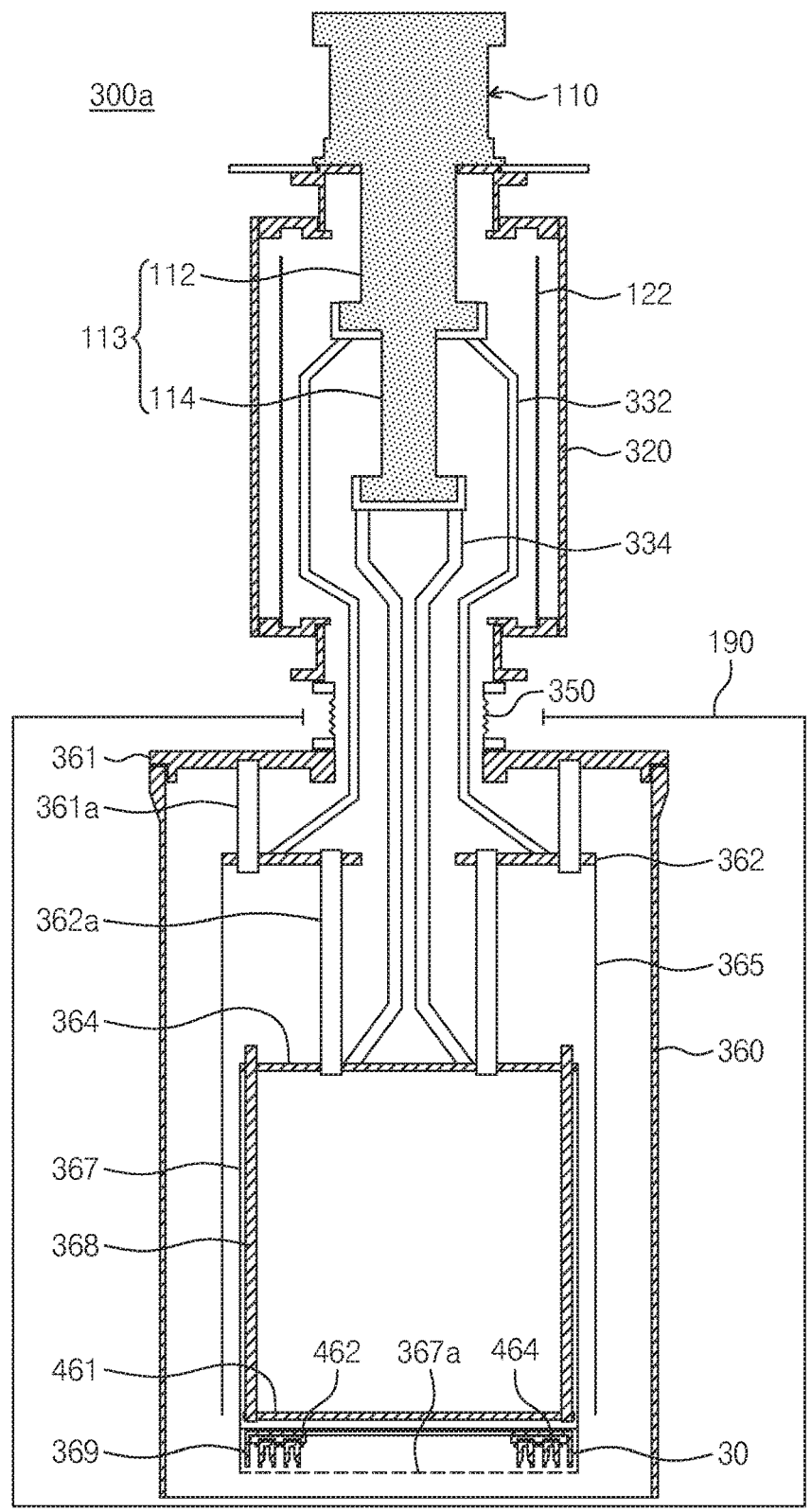
FIG. 12 illustrates a SQUID system according to another example embodiment of the present disclosure.

FIG. 12 illustrates a SQUID system according to another example embodiment of the present disclosure. In FIG. 12, the same components or parts as those shown in FIGS. 1 through 11 are designated with the same numerals and their explanations will be omitted.

Referring to FIG. 12, a cryocooler superconducting quantum interference device (SQUID) system 300a includes a cryocooler 110 including a cold head 113, a cold head chamber 113 in which the cold head 113 is disposed, a sensor chamber 360 including a SQUID sensor 30 cooled to a low temperature by the cryocooler 110, and a connection block 350 connecting the cold head 113 and a thermal anchor disposed in the sensor chamber 360 to each other to cool the SQUID sensor 30 in the sensor chamber 360. The connection block 350 may be a bellows tube.

The cold head chamber 320 may be disposed outside a magnetically shielded room 190, and the sensor chamber 360 may be disposed inside the magnetically shield room 190.

Returning to FIG. 10, we proposed a cryocooled SQUID system 300 measuring an MCG and an MEG. To reduce a cyclic magnetic noise caused by a regenerator of a cold head, a superconductive shield is used to protect the SQUID sensor 30 and a ferromagnetic cold head shield 122 is used to screen the cold head 113.

The sensor chamber 360 may be spaced apart from the cold head chamber 320 by a distance of 1.8 meter. The cold head chamber 360 may be disposed inside a magnetically shield room (MSR). Resulting from the increased distance, loss of cooling power is compensated by increasing the number of thermal rods. Thus, the SQUID sensor 30 and the superconductive shield 369 may be cooled to temperatures of 4.8 K and 5 K, respectively. The superconductive shield 369 may remover a thermal noise emitted from a metal block used to increase thermal transfer. A noise of the SQUID system was 3 $fT/Hz^{1/2}$, and a cyclic magnetic noise was reduced to approximately 1.7 pT. As a result, a clean MCG signal may be obtained without special signal processing while the entire cooling system operates.

In an example embodiment of the present disclosure, we propose a closed-cycle cryocooled SQUID system including a superconductive shield and a ferromagnetic shield to measure a biomagnetic signal.

We use a superconductive shield for a SQUID sensor and use a ferromagnetic shield for a regenerator (Er3Ni) of a cryocooler to reduce a thermal noise and a cyclic magnetic noise.

Continuing to refer to FIG. 10, the cryocooler 110 is used to cool the SQUID sensor 30 and the superconductive shield 369. The superconductive shield 369 may remove all thermal noises in the whole frequency domain. Accordingly, we may use a solid heavy thermal rod to cool the SQUID system 300. Additionally, we may separate the cold head chamber 320 and the sensor chamber 360 from each other. The cold head chamber 320 may be mounted inside or outside a magnetically shielded room (MSR). A magnetic noise generated from a cryocooler mounted outside the MSR may be further reduced.

We have investigated dependency of cooling characteristics to a length of a thermal rod. We measured a white noise and a cyclic magnetic noise depending on whether shielding exists or not. To evaluate the cryocooled SQUID system, we measured an MCG signal using two types of SQUID systems.

[Superconductive Shield]

To determine a distance between the SQUID sensor 30 and the superconductive shield 369, we measured a shielding factor with respect to two different shapes of the superconductive shield 369 as a distance function.

Figure 13:
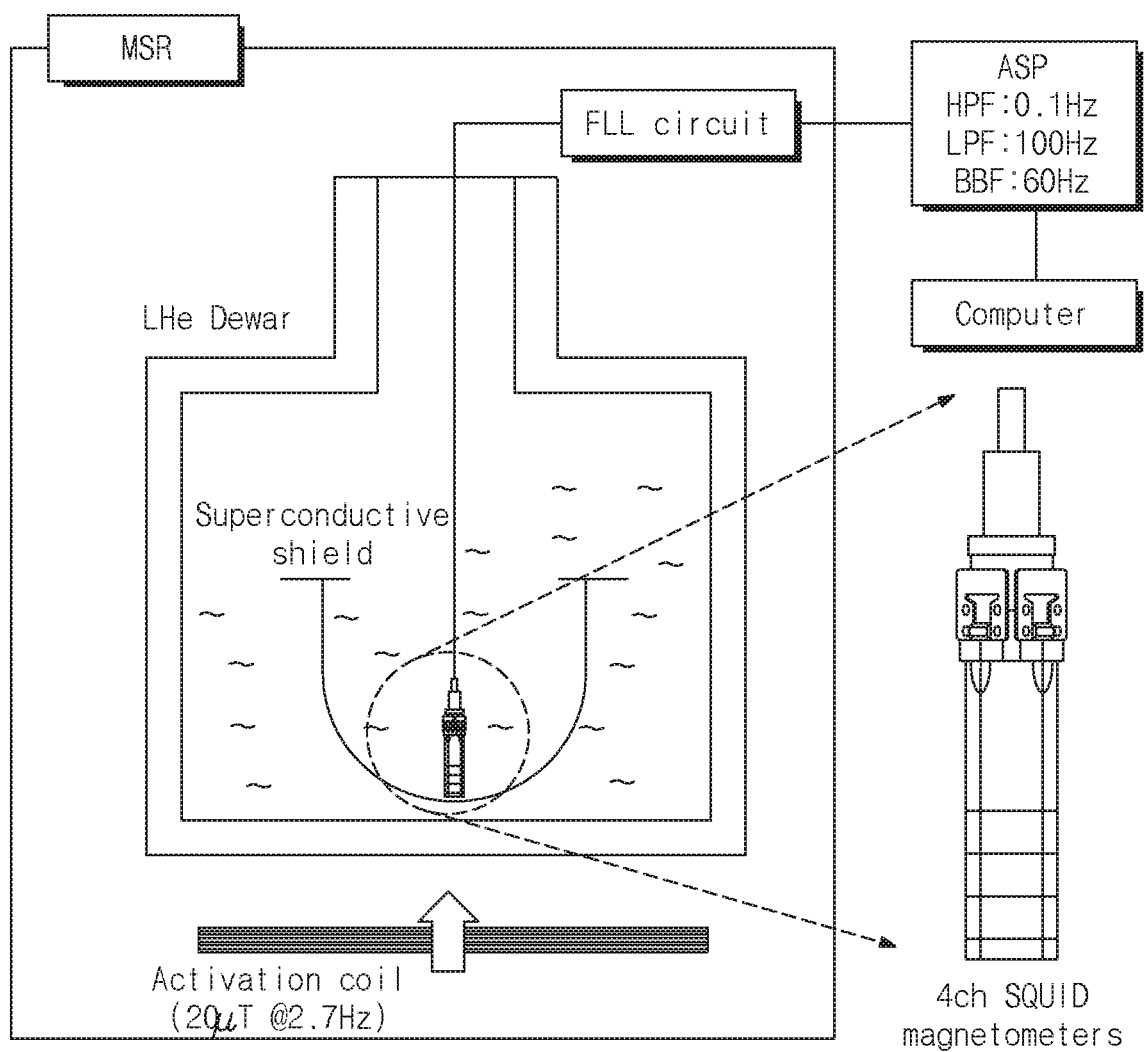
FIG. 13 illustrates the configuration of a superconductive shield surrounding a SQUID sensor array under an applied magnetic field.

FIG. 13 illustrates the configuration of a superconductive shield surrounding a SQUID sensor array under an applied magnetic field.

Referring to FIG. 13, we mounted four SQUID magnetometers each including a pick-up coil having a diameter of 20 millimeters (mm) to a shielding factor depending on a distance between a pick-up coil and a superconductive shield.

An NbTi wire having a diameter of 120 micrometers is wound on a bobbin for a pick-up coil. A distance between the pick-up coil and the superconductive shield is maintained by 5, 15, 25, 35, and 45 mm. The bobbin on which the pick-up coil is wound is warped by 45 mm to measure a magnetic field at 45 mm. The superconductive field is cooled by liquid helium. An activated coil having a diameter of 600 mm is disposed to be spaced apart from a bottom surface of the cooling system by 50 mm. The shielding factor decreases exponentially as the distance between the pick-up coil and a surface of the superconductive shield increases.

Figure 14:
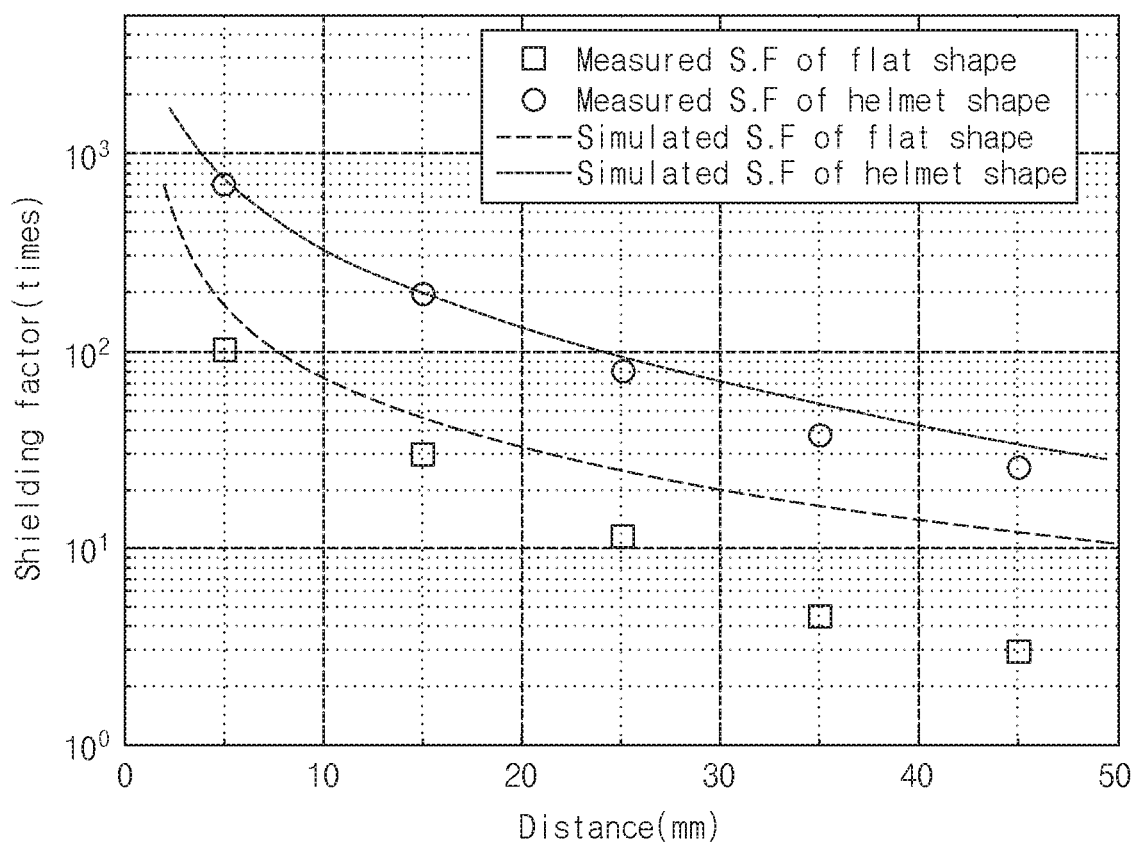
FIG. 14 illustrates a shielding factor of the superconductive shield as a function of distance.

FIG. 14 illustrates a shielding factor of the superconductive shield as a function of distance.

Referring to FIG. 14, in the case of a flat-plate superconductive shield, a magnetic field decreases by $1/100$, $1/11$, and $1/3$ at 5 mm, 25 mm, and 45 mm, respectively.

A helmet-shaped superconductive shield has a shielding factor that is eight times higher than a flat-plate shielding factor.

Variation of a magnetic field established by a current source induces Meissner current. The Meissner current may be considered a result of an image current source having an opposite sign of a magnetic field component perpendicular to the boundary of a superconductor. Accordingly, in a SQUID magnetometer, superposition of a magnetic field may be the same as a gradiometer coil where one loop is disposed at the SQUID magnetometer and the other loop is disposed on an image plane. A distance of the gradiometer coil may be two times longer than a distance between the boundary of the superconductor and the SQUID magnetometer. Since a baseline of a pick-up coil is determined by depth of a biomagnetic signal source, we adapted a distance of 25 mm between the pick-up coil and a surface of the superconductor. Thus, a superconductive imaging baseline is 50 mm.

[Configuration of System]

Returning to FIG. 10, the SQUID system 300 includes a 13-channel SQUID sensor 30, optical-based electronics for controlling the SQUID sensor 30 and transmitting data to a computer, a superconductive shield 369, a cold head shield 122, and a cooling system. We use a double-relaxation oscillation SQUID (DROS) to measure a biomagnetic signal.

The pick-up coil is disposed to be spaced apart from a superconductive shield by 25 mm. A flux-locked loop (FLL) is electrically isolated from a data acquisition computer. An acquired analog signal is converted into a digital signal by an analog-digital converter.

To compare a conventional cryocooled SQUID system with a cryocooled SQUID system according to an example embodiment of the present disclosure, we configured two types of closed-cycle SQUID systems including a flat-plate superconductive shield.

In the conventional cryocooled SQUID system, a cold head is disposed inside a chamber of GFRP together with a SQUID sensor. Two types of SQUID sensors were used. One is a first-order gradiometer having a baseline of 50 mm, and the other is a gradiometer. The SQUID sensor is not surrounded by a superconductive shield. The integral SQUID system is mounted inside a magnetically shielded room having a shielding factor of 0.1 Hz to 40 dB.

Continuing to refer to FIG. 10, in an example embodiment of the present disclosure, thirteen SQUID sensors 30 are mounted on a G10 plate in a separated cryocooled SQUID system. The G10 plate is surrounded by the flat-plate superconductive shield 369 to check characteristics of superconductive shielding and ferromagnetic shielding. The SQUID sensor 30 is disposed in the center, middle, and edge of the superconductive shield 369 to observe a white noise and a cyclic magnetic noise. The sensor chamber 360 in which the SQUID sensor 30 is disposed is separated from the cold head chamber 320 in which a cryocooler is disposed. The SQUID sensor 30 is a magnetometer shielded by a shielding plate having a brim of 30 mm. The cold head chamber 320 is shielded by three-folded Mu-metal having a thickness of 0.1 mm. The cold head chamber 320 may be connected to the sensor chamber 360 through the connection block 350 including a bellows tube to reduce a vibration. The cold head chamber 320 and the sensor chamber 360 may be mounted inside the magnetically shielded room 190. The separated SQUID system is mounted inside the magnetically shielded room having a shielding factor of 0.1 Hz to 40 dB.

Still referring to FIG. 10, in the separated cryocooled SQUID system, a braided cooper wire is used as a thermal transfer portion to thermally connect the cold head 113 and the SQUID sensor 30 to each other. The cold head 113 includes a first stage cold head 112 and a second stage cold head 114. The first stage cold head 112 is connected to a 40 K thermal anchor by the braided copper wire, and the second stage cold head 114 is connected to a thermal anchor of 4 K by the braided copper wire. The 40 K thermal anchor may be connected to a cylindrical first thermal shield 365 of an aluminum material. The thermal anchor of 4 K may be connected to a cylindrical second thermal shield 367 of a copper material. The thermal anchor of 4 K may be disposed in the center of the sensor chamber 360.

A length of the braided copper wire is fixed to 450 mm in the case of the integral type and may change from 450 mm to 1800 mm in the case of the separated type.

A thermal conductance may vary depending on a length of a thermal rod. Accordingly, we the number of braided copper wires increased from 8 to 32 as the length of the thermal rod increases from 450 mm to 1800 mm.

To reduce radiant heat loss increasing with the length of the thermal rod, two-layered superconductor and polyester net were mounted between the 4 K thermal rod and the 40 K thermal rod and between the first thermal shield 365 and a wall of the sensor chamber 360. Each layer has a vacuum space of 5 mm and includes 15 sets of superinsulator and polyester net.

The pick-up coil is wounded on a G10 epoxy bobbin. The pick-up coil spaced apart from the sensor cooling plate 461 by 25 mm is not cooled below 6 K. We mounted a 4 K thermal cap 367 connected to the second stage cold head 114 to cover the SQUID sensor 30.

A white noise and a cyclic magnetic noise were measured with respect to the SQUID sensor surrounded by the superconductive shield 369. The white noise and the cyclic magnetic noise were compared with a noise level for a system that does not include the superconductive shield 369. A shielding factor depending on a diameter and a temperature of the cold head shield 122 was measured to evaluate cylindrical ferromagnetic shielding for the cold head 113.

[Cooling Characteristics]

In a separated cryocooled SQUID system including a 4 K thermal rod of 450 mm, the pick-up coil of the SQUID sensor was cooled to a temperature of 5.3 K. However, it is difficult to cool the superconductive shield 369 surrounding the SQUID sensor to a temperature of 7 K or less. We attached an enamel-coated copper mesh to a surface of the superconductive shield 369 to improve thermal transfer. The attached copper mesh is connected to the 4 K thermal anchor. Thus, the temperatures of the SQUID sensor 30 and the superconductive shield 369 reached 5.3 K within one day.

As the length of the 4 K thermal rod increases from 450 mm to 1800 mm, the temperature linearly increases from 5.3 K to 24 K. A thermal conductance is defined as follows: U=kA/L (k being a thermal conductivity, A being a sectional area, and L being a length). The number of braided copper wires for the 4 K and 40 K thermal rods increased.

Figure 15:
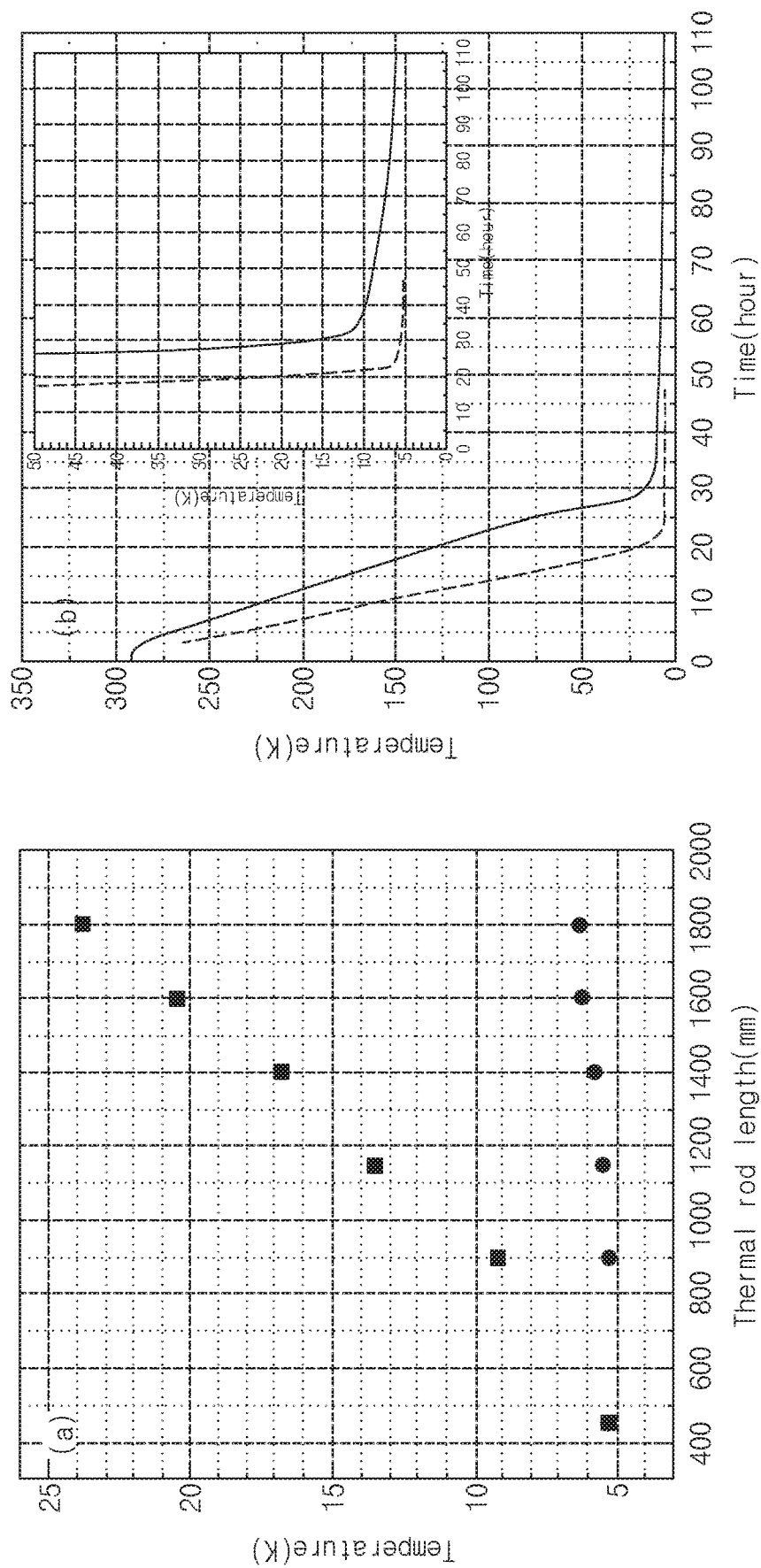
FIG. 15 illustrates a temperature of a pick-up coil.

FIG. 15 illustrates a temperature of a pick-up coil.

Referring to FIG. 15, in all the cases, temperatures of a SQUID sensor and a superconductive shield rapidly decrease to 10 K but slowly decrease at 10 K or less.

As a length of a thermal rod or a thermal transfer portion increases, a temperature of a pick-up coil increases. However, if the total diameter of braided wires constituting the thermal rod increases, the temperature of the pick-up coil is constantly maintained even when the length of the thermal rod increases.

[System Noise]

A cyclic magnetic noise generated from a compressor is 220 nT at a distance spaced apart from the compressor. The magnetic noise exponentially decreases as the distance increases. A motor valve generates a magnetic noise of 20 nT.

A shielding factor of a magnetically shield room is given. The shielding factor of the magnetically shielded room may be greater than 72 dB at 2 Hz. A magnetic noise measured by the SQUID sensor depends on a shape of the superconductive shield and should be smaller than 500 fT and 100 fT. The compressor and the motor valve are disposed outside the magnetically shielded room.

Figure 16:
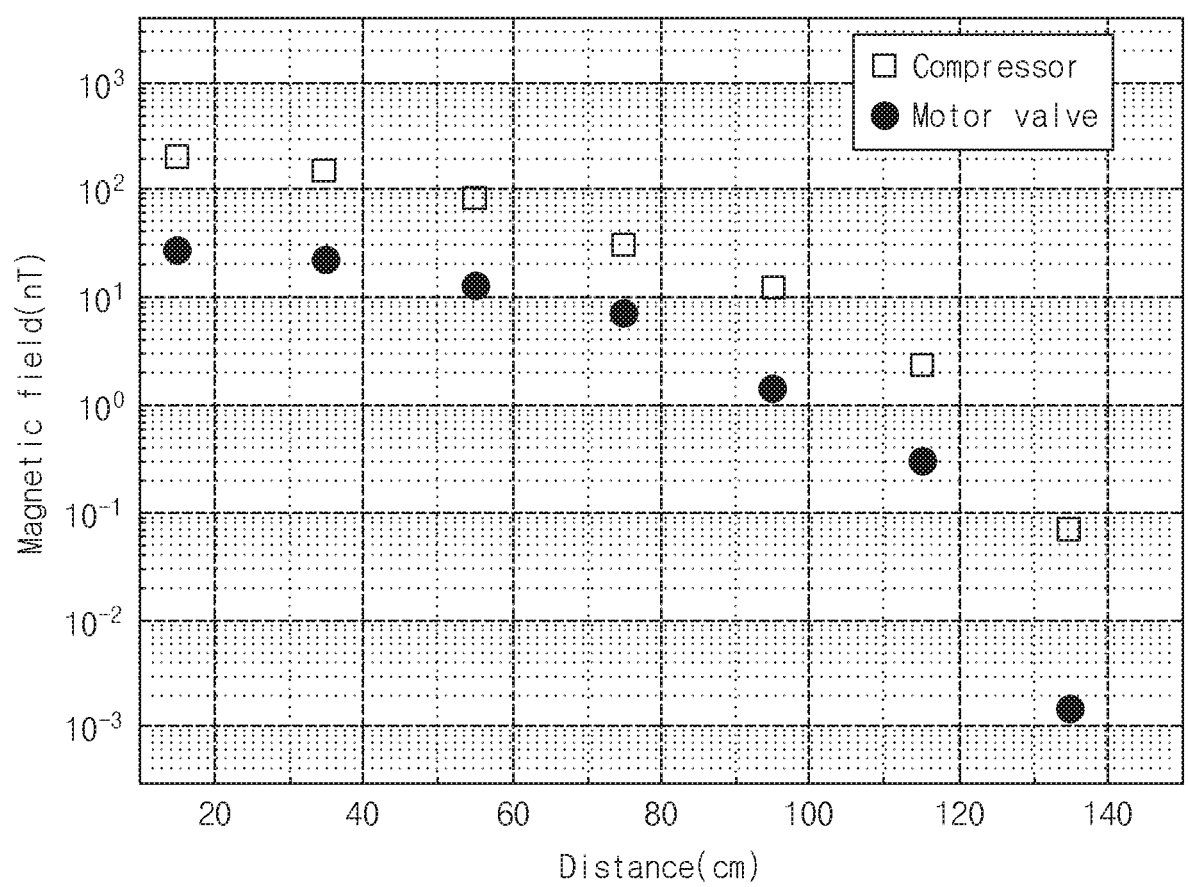
FIG. 16 illustrates a cyclic magnetic noise of a cryocooler.

FIG. 16 illustrates a cyclic magnetic noise of a cryocooler.

Referring to FIG. 16, a cold head 113 mounted in a magnetically shielded room 190 generates a cyclic magnetic noise of 20 microteslas (μT). A background noise rapidly increases at 50 Hz or less due to a chamber vibration. The cyclic magnetic noise and the vibration may generate a 1 Hz harmonic noise.

We mounted a three-folded cylindrical Mu-metal at an outer side of the cold chamber 320 to reduce the cyclic magnetic noise. A Mu-metal cylinder is a cold head shield 122. An axis-directional magnetic noise measured at a position spaced apart from a regenerator by 140 mm is 250 nT. After the cylindrical Mu-metal is mounted at the outer side of the cold head chamber 320, a magnetic field was reduced to 900 pT.

In the case that a Mu-metal cylinder having a diameter of 170 mm is mounted inside the cold head chamber 320, a shielding factor varies depending on a temperature.

Figure 17:
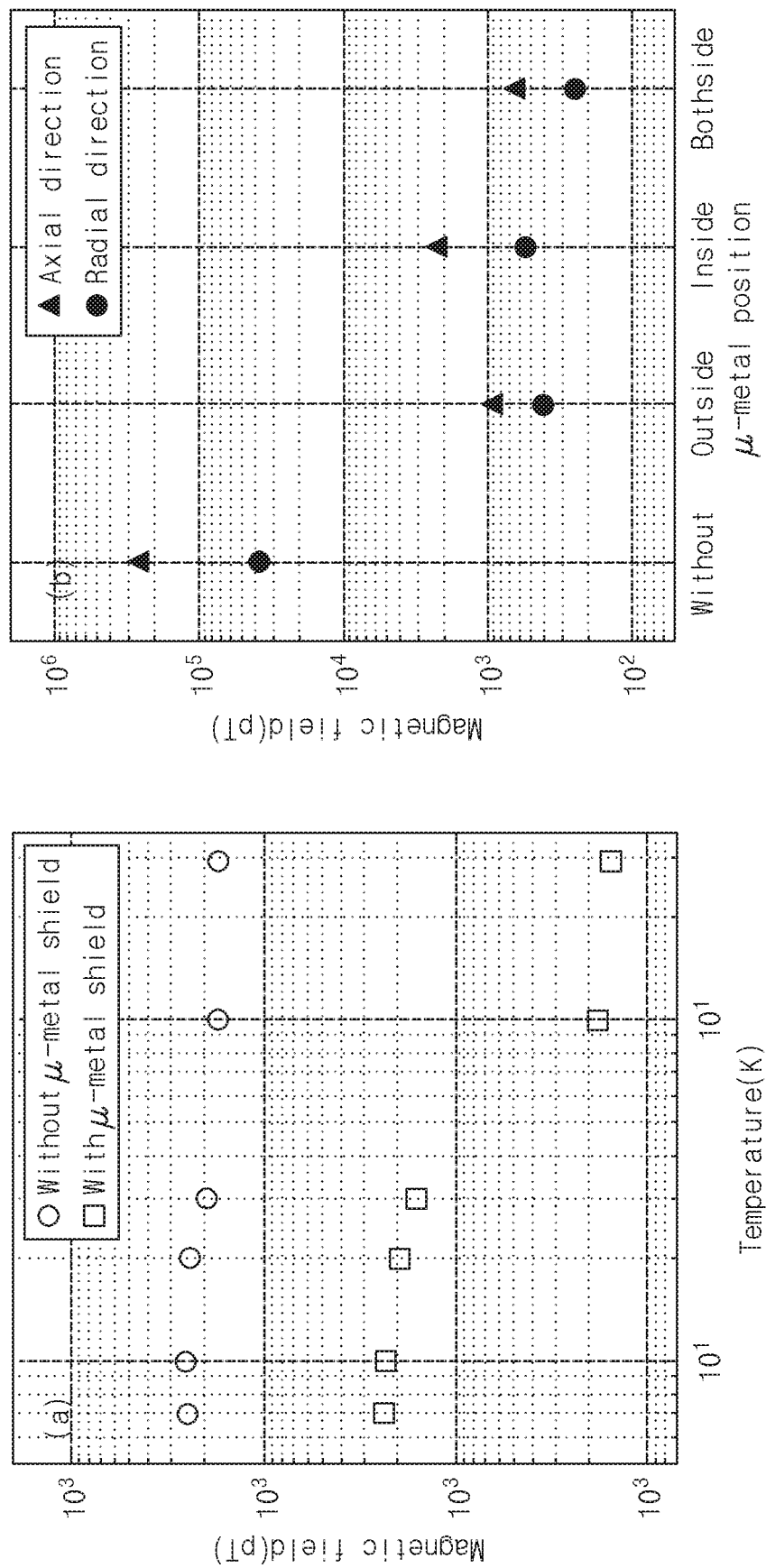
FIG. 17 illustrates a magnetic field established by a cold head depending on a position and a temperature of Mu-metal.

FIG. 17 illustrates a magnetic field established by a cold head depending on a position and a temperature of Mu-metal.

Referring to FIG. 17, numerical analysis of distribution of a magnetic field was performed to obtain shielding factors of cylindrical Mu-metals having diameters of 170 mm and 280 mm. According to the numerical analysis, the shielding factor of the Mu-metal having a diameter of 170 mm and being mounted inside is 100 times greater than that of the Mu-factor having a diameter of 280 mm and being mounted outside.

However, according to a test result, the Mu-metal mounted inside has a lower shielding factor than the Mu-metal mounted outside. The Mu-metal having a diameter of 170 mm is mounted between a 40 K thermal shield and the cold head chamber. A vacuum space and 15 sets of superinsulation layers are mounted between the Mu-metal and the 40 K thermal shield to suppress heat radiation. In this case, a temperature of the Mu-metal is 100 K. After the Mu-metal of 170 mm is mounted, an axial magnetic field decreased from 200 pT to 70 pT around the SQUID sensor.

We expected that a thermal noise generated from a metal used as a thermal shield, a thermal anchor, and a thermal rod would be completely removed by the superconductive shield. A copper mesh for a 4 K thermal cap is formed of a wire having a diameter of 80 mm. The wire is coated with enamel to be insulated. At a side surface that is not protected by the superconductive shield, a thermal noise emitted from the thermal cap does not affect a SQUID system. A white noise of the SQUID system including the superconductive shield is 3 fT/Hz$^{1/2}$ at 100 Hz. The noise level is similar to a noise level of an MEG system cooled by liquid helium.

However, a white noise measured using SQUID magnetometers and gradiometers without the superconductive shield is approximately 10 fT/Hz$^{1/2}$ and 15 fT/Hz$^{1/2}$ by a metal thermal shield and a thermal anchor.

We measured a noise in a turned-off state of a cryocooler to analyze a system noise without interference of a cyclic magnetic noise of the cryocooler. A white noise at 100 Hz is similar to a noise in an operating state. A background noise of 1 Hz to 100 Hz is lower than 5 fT/Hz$^{1/2}$.

At 10 minutes after the cryocooler was stopped, the noise level jumped to 10 fT/Hz$^{1/2}$ and an operation of the SQUID sensor was unstable. At the same time, a temperature of the superconductive shield increased to 8 K. At 15 minutes after the cryocooler was stopped, the SQUID sensor did not operate.

Figure 18:
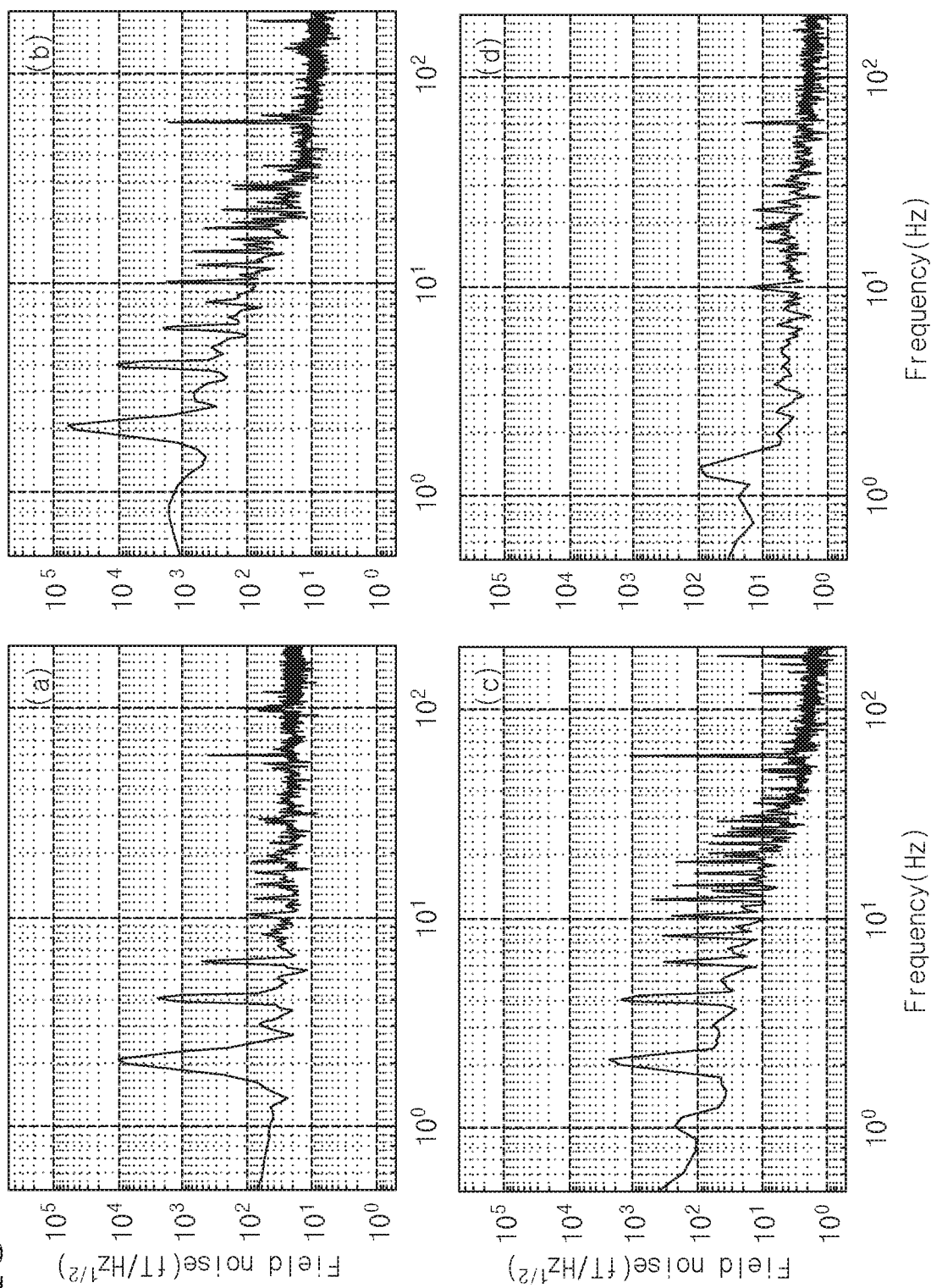
FIG. 18 illustrates a system noise spectrum according to whether there is a superconductive shield, under conditions of separating a sensor chamber and a cold head chamber and mounting Mu-metal.

FIG. 18 illustrates a system noise spectrum according to whether there is a superconductive shield, under conditions of separating a sensor chamber and a cold head chamber and mounting Mu-metal.

Referring to FIG. 18, (a) is a measurement result of a gradiometer without superconductive shielding, (b) is a measurement result of a magnetometer without superconductive shielding, (c) is a measurement result of a magnetometer with superconductive shielding, and (d) is a spectrum of a signal measured by a magnetometer with superconductive shielding.

A cyclic magnetic noise measured using SQUID magnetometer and gradiometer without superconductive shielding is 80 pT and 10 pT, respectively. However, in the case of having superconductive shielding, the magnetic noise is 1.7 $pT/Hz^{1/2}$ in the center, 3 $pT/Hz^{1/2}$ in the middle, and 8 $pT/Hz^{1/2}$ at the edge. A magnetic noise measured by a magnetometer having a 50 mm superconductive imaging baseline was smaller than a magnetic noise measured by a gradiometer having a 50 mm baseline. A gradiometer having a geometric structure has a balance factor with respect to a uniform magnetic field. However, a magnetic noise emitted by the cryocooler is non-uniform. The SQUID gradiometer does not effectively reduce the magnetic noise emitted by the cryocooler. However, a background noise of 40 Hz or less is effectively shielded by the SQUID gradiometer.

Figure 19:
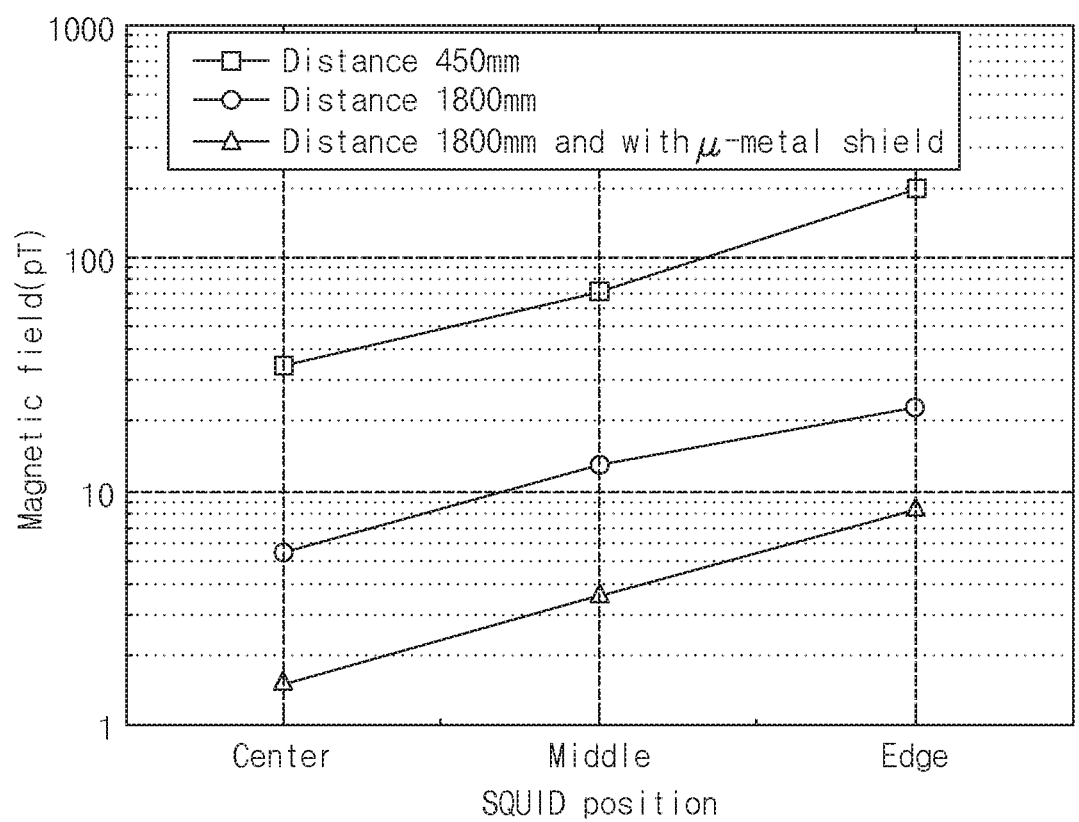
FIG. 19 illustrates magnetic noise reduction depending on separation between a SQUID chamber and a cold head chamber and the effect of Mu-metal.

FIG. 19 illustrates magnetic noise reduction depending on separation between a SQUID chamber and a cold head chamber and the effect of Mu-metal.

Referring to FIG. 19, we compared reductions in a magnetic noise to evaluate chamber separation and effect of Mu-metal under superconductive shielding. The magnetic noise decreased by eight times in the case that a cold head chamber is spaced apart from a sensor chamber by 1800 mm. In addition, the magnetic noise decreases by three times in the case that Mu-metal is mounted at an outer side of the cold head after the cold head chamber is separated from the sensor chamber.

[MCG Signal]

We measured an MCG signal by using a cryocooled SQUID magnetometer having superconductive shielding and ferromagnetic shielding. We also measured an MCG signal with respect to the same target by using magnetometer and first-order gradiometer SQUID system without superconductive shield. The SQUID system includes an analog signal processor having a bandpass filter of 0.1 to 100 Hz.

Figure 20:
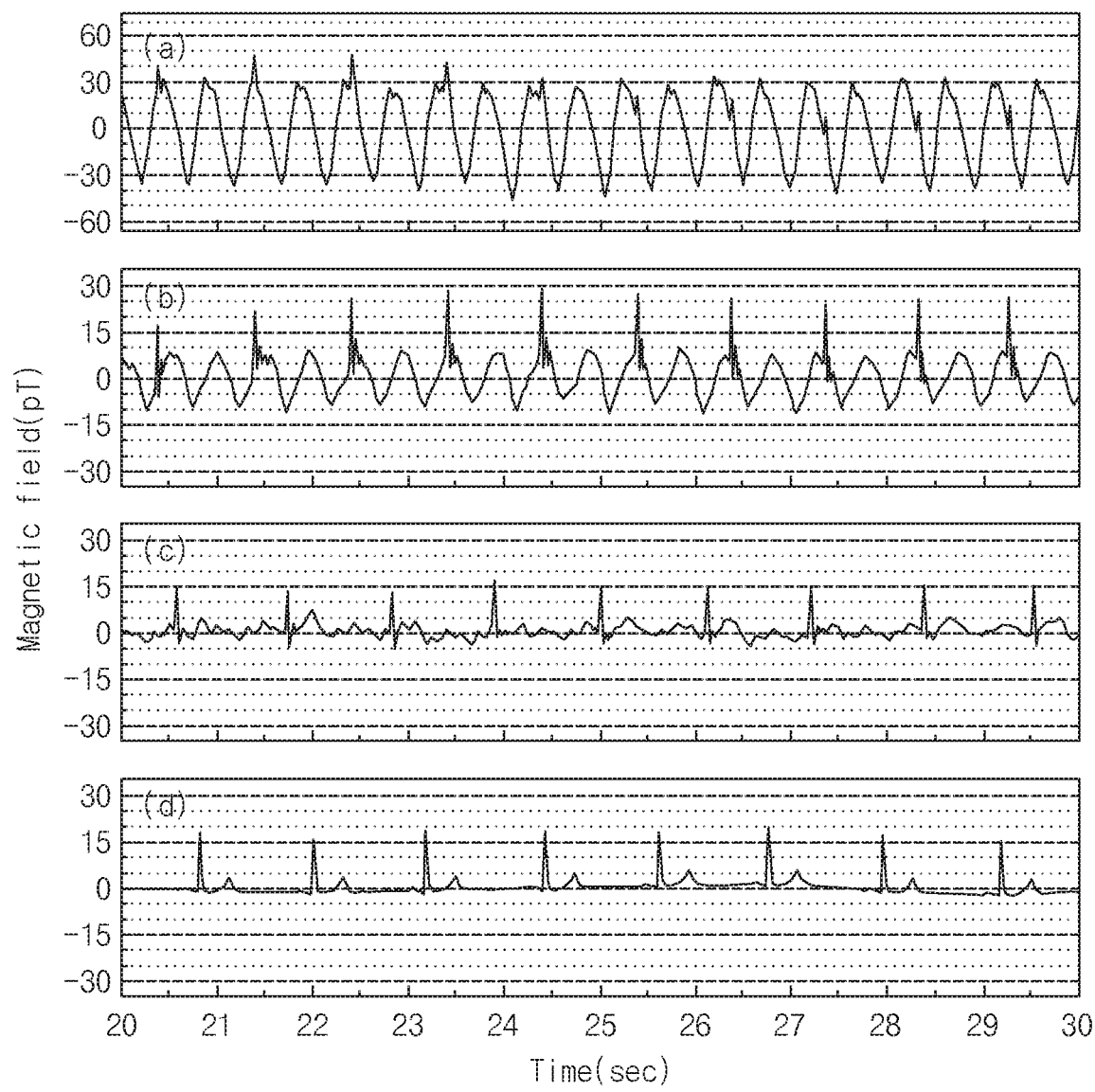
FIG. 20 illustrates a real-time signal.

FIG. 20 illustrates a real-time signal.

Referring to FIG. 20, magnetic noises measured by third type of SQUID system were 2.5 $pT_{p-p}$, 15 $pT_{p-p}$, and 60 $pT_{p-p}$. A cyclic magnetic noise measured by a first-order gradiometer and a magnetometer was severely distorted after five times averaging.

However, we are capable of obtaining a pattern of an MCG signal by using superconductive shielding. The intensity of the MCG signal measured by a SQUID sensor disposed in the center of a sensor mounting plate is low because it is directly on main myocardial current.

An MCG signal disposed at the corner circumference of a superconductive shield is distorted by a stray magnetic field established by Meissner effect. After turning off a cryocooler, we measured the MCG signal to check superconductive shielding and temperature holding time of a SQUID system. We were capable of obtaining a clear MCG signal for 10 minutes after turning off the cryocooler.

We showed that cryocooled shielding and ferromagnetic shielding operated efficiently in a closed-cycle cryocooled SQUID system. A thermal noise and a cyclic magnetic noise emitted from the cryocooler were reduced using two shields to measure biomagnetic signals.

According to an example embodiment of the present disclosure, a SQUID was directly cooled using a pulse-type (PT) cryocooler. To remove a cyclic magnetic noise, a SQUID sensor used superconductive shielding and a cryocooler used ferromagnetic shield. To minimize an influence of a magnetic noise generated from the cryocooler, a cold head chamber for the cryocooler and a sensor chamber for the SQUID sensor are separated from each other.

In addition, a vibration and a magnetic noise were minimized by connecting to a bellows tube for vacuum absorption. Moreover, an optimal method of preventing radiant heat is proposed for effective cooling of a SQUID sensor separated from a cold head by 1.8 meter. Noise characteristics and cooling characteristics of a manufactured SQUID system were evaluated, and an MEG signal and an MCG signal were satisfactorily measured.

Although the present disclosure and its advantages have been described in detail, it should be understood that various changes, substitutions and alterations can be made herein without departing from the spirit and scope of the disclosure as defined by the following claims.

What is claimed is:

1. A cryocooler superconducting quantum interference device (SQUID) system comprising:
   a cryocooler including a cold head;
   a cold head chamber in which the cold head is disposed;
   a sensor chamber including a SQUID sensor cooled to a low temperature by the cryocooler; and
   a connection block connecting the cold head and a thermal anchor disposed in the sensor chamber to each other to cool the SQUID sensor in the sensor chamber;
   wherein the cryocooler is a pulse tube cryocooler, and
   the cryocooler includes a first stage cold head cooled to a first temperature (40 K) and a second stage cold head cooled to a second temperature (4 K);
   further comprising:
   a tube-shaped thermal transfer tube disposed inside the connection block and connecting the first cold head and a first thermal anchor disposed in the sensor chamber to each other; and
   a rod-shaped thermal transfer rod disposed inside the thermal transfer tube and connecting the second stage cold head and a second thermal anchor disposed in the sensor chamber to each other.

2. The cryocooler SQUID system of claim 1, further comprising:
   a cold head magnetic shield formed of permalloy disposed to surround the cold head inside or outside the cold head chamber.

3. The cryocooler SQUID system of claim 1, wherein the connection block comprises:
   a first elbow block connected to the cold head chamber;
   a straight block connected to the first elbow block;
   a second elbow block connected to the straight block;
   an elbow-shaped first thermal transfer tube disposed inside the first elbow block and the straight block;
   an L-shaped first thermal transfer rod disposed inside the first thermal transfer tube and the straight block;
   an elbow-shaped second thermal transfer tube disposed inside the second elbow block; and
   an L-shaped second thermal transfer rod disposed inside the second thermal transfer tube,
   wherein the second elbow block is connected to the sensor chamber.

4. The cryocooler SQUID system of claim 3, wherein the first thermal transfer tube and the second thermal transfer tube are connected by a braided copper wire, and
   the first thermal transfer rod and the second thermal transfer rod are connected by a braided copper wire.

5. The cryocooler SQUID system of claim 4, further comprising:

a rotation flange disposed at a portion where the first thermal transfer tube and the second thermal transfer tube are connected to each other and providing a rotational motion to the second elbow block and the sensor chamber fixed to each other.

6. The cryocooler SQUID system of claim 4, wherein one end of the rotation flange is in a form of a tapered tube inserted into the straight block, and a groove is formed on a surface of the tapered tube to maintain a vacuum state.

7. The cryocooler SQUID system of claim 1, further comprising:

an internal adiabatic layer disposed between the thermal transfer rod and the thermal transfer tube; and an external adiabatic layer disposed between the thermal transfer tube and the connection block.

8. The cryocooler SQUID system of claim 1, further comprising:

a space maintaining portion formed of an adiabatic material and disposed between the thermal transfer rod and the thermal transfer tube to maintain a fixed distance.

9. The cryocooler SQUID system of claim 8, wherein the space maintaining portion comprises:

a pair of star-shaped spacers inserted into opposite ends of a straight portion of the thermal transfer rod; and a plurality of rod-shaped spacer supports connecting the pair of spacers to each other.

10. A cryocooler superconducting quantum interference device (SQUID) system comprising:

a cryocooler including a cold head;

a cold head chamber in which the cold head is disposed;

a sensor chamber including a SQUID sensor cooled to a low temperature by the cryocooler; and a connection block connecting the cold head and a thermal anchor disposed in the sensor chamber to each other to cool the SQUID sensor in the sensor chamber, wherein the cryocooler is a pulse tube cryocooler, and wherein the cryocooler includes a first stage cold head cooled to a first temperature (40 K) and a second stage cold head cooled to a second temperature (4 K), further comprising:

a washer-shaped first thermal anchor disposed in the sensor chamber and connected to the thermal transfer tube;

a washer-shaped second thermal anchor disposed in the sensor chamber and connected to the thermal transfer rod;

a cylindrical first thermal shield connected to the first thermal anchor and extending in a central axis direction of the sensor chamber; and a cylindrical second thermal shield disposed inside the first thermal shield, connected to the second thermal anchor, and extending in the central axis direction of the sensor chamber.

11. The cryocooler SQUID system of claim 10, further comprising:

a pair of washer-shaped auxiliary thermal anchors disposed between the first thermal anchor and the second thermal anchor; and an auxiliary thermal transfer portion inserted between the pair of auxiliary thermal anchors to extend in the central axis direction of the sensor chamber and formed of a copper mesh.

12. The cryocooler SQUID system of claim 1, further comprising:

a superconductive shield disposed around the SQUID sensor to remove an external noise and formed of a superconductor.

13. The cryocooler SQUID system of claim 1, wherein the cold head chamber accommodating the cold head is separated from the sensor chamber accommodating the SQUID sensor.

14. The cryocooler SQUID system of claim 1, wherein the cold head chamber, the connection block, and the sensor chamber are maintained in a vacuum state.

15. A cryocooler superconducting quantum interference device (SQUID) system comprising:

a cryocooler including a cold head;

a cold head chamber in which the cold head is disposed;

a sensor chamber including a SQUID sensor cooled to a low temperature by the cryocooler; and a connection block connecting the cold head and a thermal anchor disposed in the sensor chamber to each other to cool the SQUID sensor in the sensor chamber, wherein the superconductive shield is in a form of a helmet, and which further comprises:

a SQUID sensor-mounted helmet disposed inside the superconductive shield;

a first thermal cap cooled to a temperature of 40 K, disposed to cover the SQUID sensor, and formed of a copper mesh molded in the form of a helmet; and a second thermal cap cooled to a temperature of 4 K, disposed between the first thermal cap and the SQUID sensor-mounted helmet, and formed of a copper mesh molded in the form of a helmet.

16. The cryocooler SQUID system of claim 15, wherein the superconductive shield comprises:

a hemispherical superconductive helmet body;

an outer brim extending from a bottom surface to an outer side of the superconductive helmet body; and an inner brim extending from the bottom surface to an inner side of the superconductive helmet body.

17. The cryocooler SQUID system of claim 1, wherein the cold head chamber is disposed outside a magnetically shielded room, and the sensor chamber is disposed inside the magnetically shield room.

18. The cryocooler SQUID system of claim 1, wherein the cold head chamber and the sensor chamber are disposed inside a magnetically shielded room.

19. The cryocooler SQUID system of claim 1, wherein the connection block is a bellows to reduce a vibration.

20. The cryocooler SQUID system of claim 1, further comprising:

a thermal transfer portion thermally connecting the cold head and the thermal anchor to each other, wherein the thermal transfer portion is flexible braided copper wires.

21. The cryocooler SQUID system of claim 20, wherein a length of the flexible braided copper wires is 1 meter or longer.

22. The cryocooler SQUID system of claim 1, wherein the first stage cold head is connected to a 40 K first thermal anchor by a first thermal transfer portion, the second stage cold head is connected to a 4K second thermal anchor by a second thermal transfer portion, and the first and second thermal transfer portions are flexible braided copper wires.

* * * * *